US012778624B2

(12) United States Patent
Mo et al.

(10) Patent No.: US 12,778,624 B2
(45) Date of Patent: Nov. 3, 2026

(54) PUNCTURE DEVICE AND SHEATH TUBE

(71) Applicant: Surgaid Medical (Xiamen) Co., Ltd., Xiamen (CN)

(72) Inventors: Yifan Mo, Xiamen (CN); Linfeng Hu, Xiamen (CN); Boze Huang, Xiamen (CN); Dekun Xu, Xiamen (CN); Congjie Lin, Xiamen (CN); Yanlan Luo, Xiamen (CN)

(73) Assignee: SURGAID MEDICAL (XIAMEN) CO., LTD., Xiamen (CN)

( * ) Notice: Subject to any disclaimer, the term of this patent is extended or adjusted under 35 U.S.C. 154(b) by 155 days.

(21) Appl. No.: 18/287,916

(22) PCT Filed: Apr. 19, 2022

(86) PCT No.: PCT/CN2022/087740
§ 371 (c)(1),
(2) Date: Oct. 23, 2023

(87) PCT Pub. No.: WO2022/222929
PCT Pub. Date: Oct. 27, 2022

(65) Prior Publication Data

US 2024/0197362 A1 Jun. 20, 2024

(30) Foreign Application Priority Data

Apr. 22, 2021 (CN) ......................... 202110438263.0
Jul. 30, 2021 (CN) ......................... 202121777407.7

(51) Int. Cl.
*A61B 17/34* (2006.01)
*A61B 17/00* (2006.01)
*A61B 90/00* (2016.01)

(52) U.S. Cl.
CPC ............ *A61B 17/34* (2013.01); *A61B 90/361* (2016.02); *A61B 2017/00398* (2013.01)

(58) Field of Classification Search
CPC ............ A61B 17/3496; A61B 17/3476; A61B 2017/349; A61B 17/3498
See application file for complete search history.

(56) References Cited

U.S. PATENT DOCUMENTS 6,432,085 B1 8/2002 Stellon et al.
2005/0267591 A1* 12/2005 Ricci ................ A61M 39/0247 623/23.44

(Continued)

FOREIGN PATENT DOCUMENTS

CN 101947121 A 1/2011
CN 104089123 A 10/2014

(Continued)

OTHER PUBLICATIONS

International Search Report for PCT/CN2022/087740 mailed Jul. 25, 2022. 6 pgs.

*Primary Examiner* — Brigid K Byrd
(74) *Attorney, Agent, or Firm* — Ladas & Parry, LLP

(57) ABSTRACT

A puncture device (1), comprising: a puncture base (10), a protective sleeve (60), a disassembling/assembling assembly (50) and a puncture assembly (40). One end of the protective sleeve (60) is provided with a mounting hole (610); the protective sleeve (60) is sleeved on the puncture base (10); the disassembling/assembling assembly (50) is connected to the end of the protective sleeve (60) having the mounting hole (610); and a tip (43) of the puncture assembly (40) sequentially passes through the disassembling/assembling assembly (50) and the mounting hole (610) to be in driving connection with the puncture base (10). Also provided is a sheath tube, comprising: a sheath tube body (11) and a first thread structure (12) and a first horizontal stripe structure (13) provided on an outer wall of the sheath tube body (11). The first thread structure (12) is provided at a first end of the sheath tube body (11); the first horizontal stripe structure (13) is provided between the first thread structure (12) and a second end (14) of the sheath tube body (11) in an axial direction of the sheath tube body (11); and horizontal stripes of the first horizontal stripe structure (13) are patterns perpendicular to the axial direction of the sheath tube body (11). After the puncture device (1) is used, it is unnecessary to spend additional time disinfecting the puncture base (10) and then disassemble/assemble the puncture assembly (40), so that the corrosion effect possibly generated by a disinfection agent on the puncture base (10) is avoided, the service life of the puncture base (10) is prolonged, and damage to a sterile environment for the puncture (Continued)

assembly (40) is avoided while quick disassembling/assembling of the puncture base (10) and the puncture assembly (40) is achieved. By using the first thread structure (12) and the first horizontal stripe structure (13), a friction force with an incision tissue is increased, thereby improving the stability of fixing the sheath tube in an incision.

18 Claims, 13 Drawing Sheets

(56) References Cited

U.S. PATENT DOCUMENTS

| | | | | |
|---|---|---|---|---|
| 2006/0165479 | A1 | 7/2006 | Lorenz | |
| 2011/0196206 | A1 | 8/2011 | Hammond | |
| 2017/0245888 | A1 * | 8/2017 | Buyda | A61B 17/3421 |
| 2018/0360460 | A1 * | 12/2018 | Mozdzierz | A61B 17/1155 |
| 2019/0350619 | A1 * | 11/2019 | Fujii | A61B 1/3132 |
| 2021/0338272 | A1 * | 11/2021 | Muthuchidambaram | A61B 17/3423 |

FOREIGN PATENT DOCUMENTS

| | | | | |
|---|---|---|---|---|
| CN | 105615957 | A | | 6/2016 |
| CN | 207020906 | U | * | 2/2018 |
| CN | 109009291 | A | | 12/2018 |
| CN | 209153878 | U | | 7/2019 |
| CN | 209172453 | U | | 7/2019 |
| CN | 212755818 | U | | 3/2021 |
| CN | 113133815 | A | | 7/2021 |
| CN | 215384486 | U | | 1/2022 |

* cited by examiner

PUNCTURE DEVICE AND SHEATH TUBE

CROSS-REFERENCE TO RELATED APPLICATIONS

The present application is a U.S. National entry under 35 U.S.C. § 371 of International Application No. PCT/CN2022/087740, filed Apr. 19, 2022, which claims the benefit of, and priority to Chinese Patent Application No. 202110438263.0 filed on Apr. 22, 2021 and Chinese Patent Application No. 202121777407.7 filed on Jul. 30, 2021 in the China National Intellectual Property Administration, the disclosures of which are hereby incorporated by reference in its entirety.

TECHNICAL FIELD

The present application relates to the technical field of medical instruments, and in particular to a puncture device and a sheath tube.

BACKGROUND

The puncture devices that are currently widely used generally have a structure that a puncture sheath and a puncture needle are combined into a puncture assembly, which is then used for surgical operations. In the prior art, the puncture assembly is connected and fixed by a reusable gun-type puncture base. However, during an operation of the puncture base, when the puncture base and the puncture assembly are assembled, the puncture base itself is prone to destroying a sterile environment for the puncture assembly, which is not conducive to clinical use.

In addition, in a surgery, in order to enable the puncture device to enter biological tissues such as an abdominal cavity, a cannula puncture device is sent into the abdominal cavity through an incision by adopting a direct torsion extrusion method or a left-right rotation extrusion method in the prior art.

However, during the puncture process, puncture strength is difficult to control; there is a very high requirement for hand control strength of a user; and the user is prone to exerting too much force, which may injure a patient and aggravate a wound of the patient. Moreover, after the puncture device enters the abdominal cavity, it is necessary to effectively fix the sheath tube at the incision. In order to avoid the user (for example, a doctor) from taking out the sheath tube when an instrument is changed and pulled out, threads of the sheath tube are usually increased to strengthen fixity of the sheath tube, or the sheath tube is fixed and sutured through a surgical suture to aggravate a damage on the incision.

SUMMARY

Aiming to the disadvantages in the existing method, the present application provides a puncture device, to be used for solving the technical problem in the prior art that during an operation of a puncture base, when the puncture base and a puncture assembly are assembled, the puncture base itself is prone to destroying a sterile environment for the puncture assembly, which is not conducive to clinical use.

An embodiment of the present application provides a puncture device, including a puncture base, a protective sleeve, a disassembling/assembling assembly and a puncture assembly, where a mounting hole is formed in one end of the protective sleeve;

the protective sleeve is sleeved on the puncture base;

the disassembling/assembling assembly is connected to one end of the protective sleeve having the mounting hole; and a tip of the puncture sequentially passes through the disassembling/assembling assembly and the mounting hole to be in driving connection with the puncture base.

Aiming to the disadvantages in the existing method, the present application provides a sheath tube, a puncture kit and a puncture device, to be used for solving the technical problem in the prior art that puncture strength of the sheath tube is difficult to control, or threads of the sheath tube are relatively large.

An embodiment of the present application provides a sheath tube, including a sheath tube body, a first thread structure and a first horizontal stripe structure, where the first thread structure and the first horizontal stripe structure are disposed on an outer wall of the sheath tube body; the first thread structure is disposed at a first end of the sheath tube body; the first horizontal stripe structure is disposed between the first thread structure and a second end of the sheath tube body in an axial direction of the sheath tube body; and horizontal stripes of the first horizontal stripe structure are patterns perpendicular to the axial direction of the sheath tube body.

The beneficial technical effects brought by the technical solutions according to the embodiment of the present application are as follows;

The puncture base is disposed in the protective sleeve, and isolated from an external environment, which provides sterile protection for the puncture base. The tip of the puncture assembly passes through the disassembling/assembling assembly and the mounting hole of the protective sleeve, to be in driving connection with the puncture base. Therefore, if there is a need for replacing different puncture assemblies for the puncture base, it is unnecessary to take down the protective sleeve, and the puncture assembly can be disassembled/assembled only through the disassembling/assembling assembly disposed outside the protective sleeve, thereby avoiding the sterile environment for the puncture assembly during a surgery from being destroyed while quickly disassembling/assembling the puncture base and the puncture assembly, and further reducing a risk of polluting the puncture base at the same time. Therefore, the puncture base can be reused, and the medical cost is lowered. It is also unnecessary to spend additional time disinfecting the puncture base and then disassemble/assemble the puncture assembly, so that the corrosion effect possibly generated by a disinfection agent on the puncture base is avoided, the service life of the puncture base is prolonged, and the efficiency of a puncturing operation is improved.

The first thread structure is disposed on the outer wall of the first end of the sheath tube extending into a patient's body. Inclined patterns have a guiding effect and can weaken a friction force during puncturing, thereby reducing the difficulty of puncturing skin tissues, and reducing the difficulty of controlling puncture strength of the sheath tube. Moreover, the first horizontal stripe structure is disposed on the outer wall between the first thread structure and the second end away from the first end, in the axial direction of the sheath tube. The friction force between the sheath tube and incision tissues is strengthened by using the horizontal patterns, which improves the stability of fixing the sheath tube on the incision. Therefore, it can effectively prevent the sheath tube from being taken out when the instrument is changed, and avoid the incision from being damaged by the increased threads of the sheath tube.

DETAILED DESCRIPTION OF THE EMBODIMENTS

The inventor of the present application has found from a study that:

In an existing puncture device, a puncture base is fixedly connected to a puncture assembly, is not removable, and can be used once only; whereas many electronic devices may be built in the puncture base, which greatly increases the medical cost. Alternatively, the existing puncture base itself has no protective measure such as a protective sleeve. Therefore, when the puncture base and the puncture assembly are assembled during a surgery, the puncture base is prone to destroying a sterile environment for the puncture assembly; and disinfection of the puncture base after use is more complicated, and thorough disinfection is difficult, and there is a risk of cross-infection when the puncture base is used secondarily. Also, a disinfection agent has a certain corrosion effect on the puncture base itself, which greatly shortens the service life of the puncture base.

Figure 1:
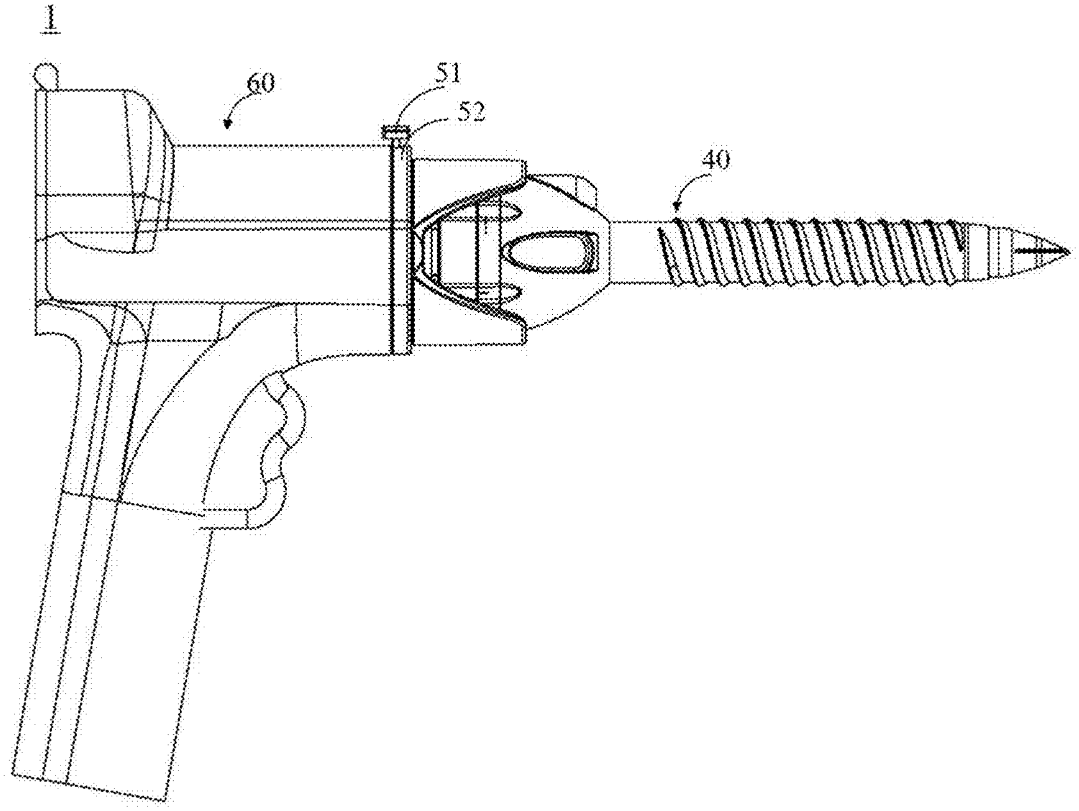
FIG. 1 is a front view of a puncture device according to an embodiment of the present application.
Figure 6:
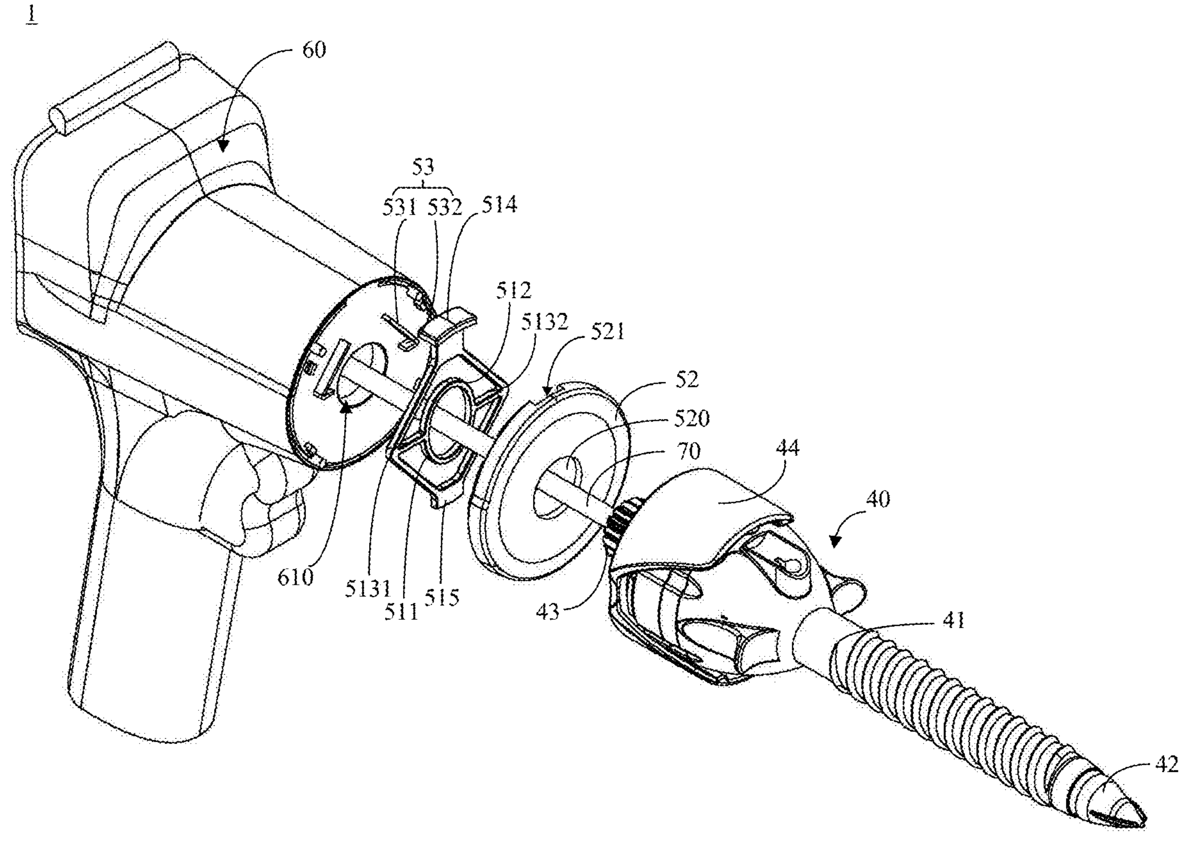
FIG. 6 is an explosion view of a puncture device according to an embodiment of the present application.

Referring to FIGS. 1 and 6, a puncture device 1 according to an embodiment of the present application includes a puncture base 10, a protective sleeve 60, a disassembling/assembling assembly 50 and a puncture assembly 40. One end of the protective sleeve 60 is provided with a mounting hole 610.

The protective sleeve 60 is sleeved on the puncture base 10.

The disassembling/assembling assembly 50 is connected to the end of the protective sleeve 60 having the mounting hole 610.

A tip 43 of the puncture assembly 40 sequentially passes through the disassembling/assembling assembly 50 and the mounting hole 610, to be in driving connection with the puncture base 10.

In this embodiment, the puncture base 10 is disposed in the protective sleeve 60, and isolated from an external environment by the protective sleeve 60, which provides sterile protection for the puncture base 10. The tip 43 of the puncture assembly 40 is drivingly connected to the puncture base 10 passing through the disassembling/assembling assembly 50 and the mounting hole 610 of the protective sleeve 60. Therefore, if there is a need for replacing different puncture assemblies 40 for the puncture base 10, it is unnecessary to take down the protective sleeve 60, and the puncture assembly 40 can be disassembled/assembled only through the disassembling/assembling assembly 50 disposed outside the protective sleeve 60, and damage to the sterile environment for the puncture assembly 40 during the surgery is avoided while quick disassembling/assembling of the puncture base 10 and the puncture assembly 40 is achieved, and a risk of polluting the puncture base 10 is also reduced. Therefore, the puncture base 10 can be reused, and the medical cost is lowered. It is also unnecessary to spend additional time disinfecting the puncture base 10 and then disassemble/assemble the puncture assembly 40, so that the corrosion effect possibly generated by a disinfection agent on the puncture base 10 is avoided, the service life of the puncture base 10 is prolonged, and the efficiency of the puncturing operation is improved.

Figure 3:
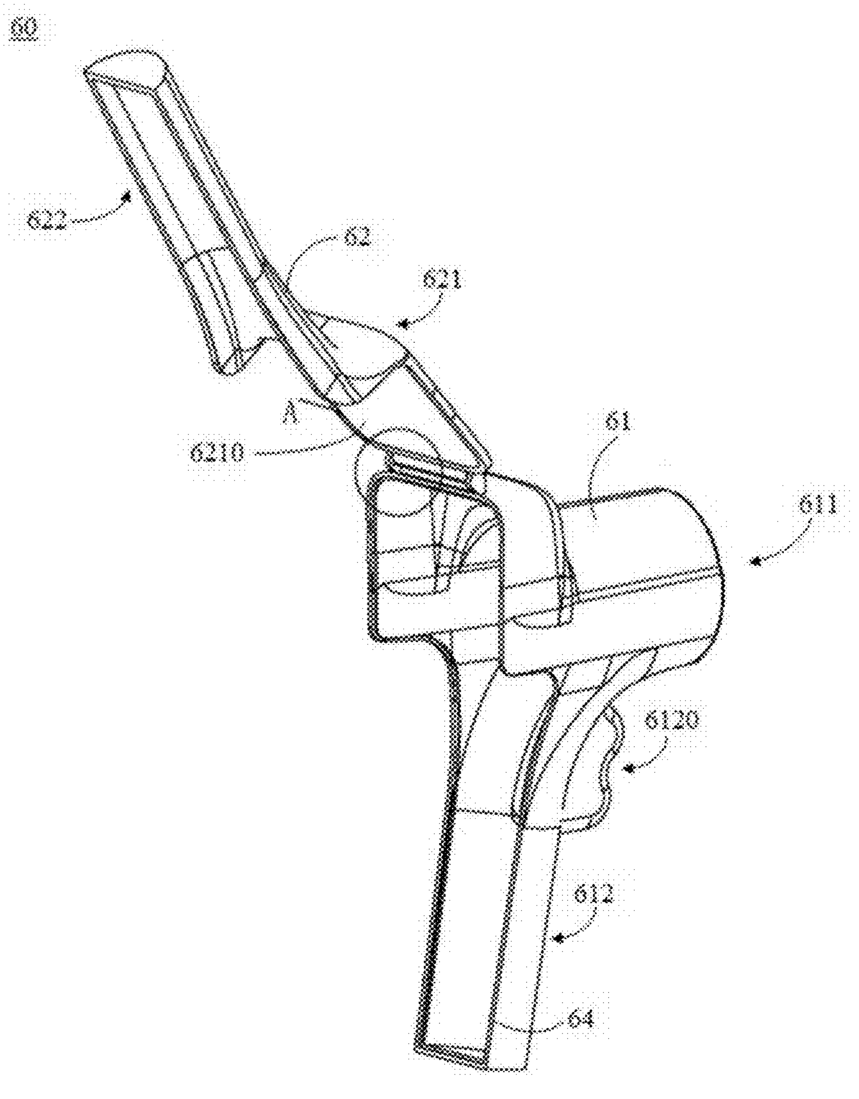
FIG. 3 is a schematic structural diagram of a protective sleeve of a puncture device before being mounted according to an embodiment of the present application.

In some possible implementations, referring to FIG. 3, the protective sleeve 60 includes a first housing 61, a second housing 62 and a moving assembly. The first housing 61 and the second housing 62 are connected through the moving assembly and coaptated to form an accommodating cavity used for accommodating the puncture base 10 in the puncture device 1. The first housing 61 is provided with a mounting hole 610, through which the tip 43 of the puncture assembly 40 in the puncture device 1 passes, to be in driving connection with the puncture base 10.

In this embodiment, the moving assembly in the protective sleeve 60 of the puncture device 1 is connected to the first housing 61 and the second housing 62; the first housing 61 and the second housing 62 are coaptated to form the accommodating cavity used for accommodating the puncture base 10 in the puncture device 1; and the first housing 61 is provided with the mounting hole 610, which is conductive to assembly between the puncture base 10 and the puncture assembly 40 of the puncture device 1. During a puncturing operation, the protective sleeve 60 of the puncture device 1 can effectively isolate the puncture base 10 from the external environment, which provides sterile protection for the puncture base 10. Therefore, the damage to the sterile environment for the puncture assembly 40 during the surgery is avoided; the risk of polluting the puncture base 10 is further greatly reduced, so that the puncture base 10 can be reused; the service life is prolonged; and the medical cost is lowered.

Figure 4:
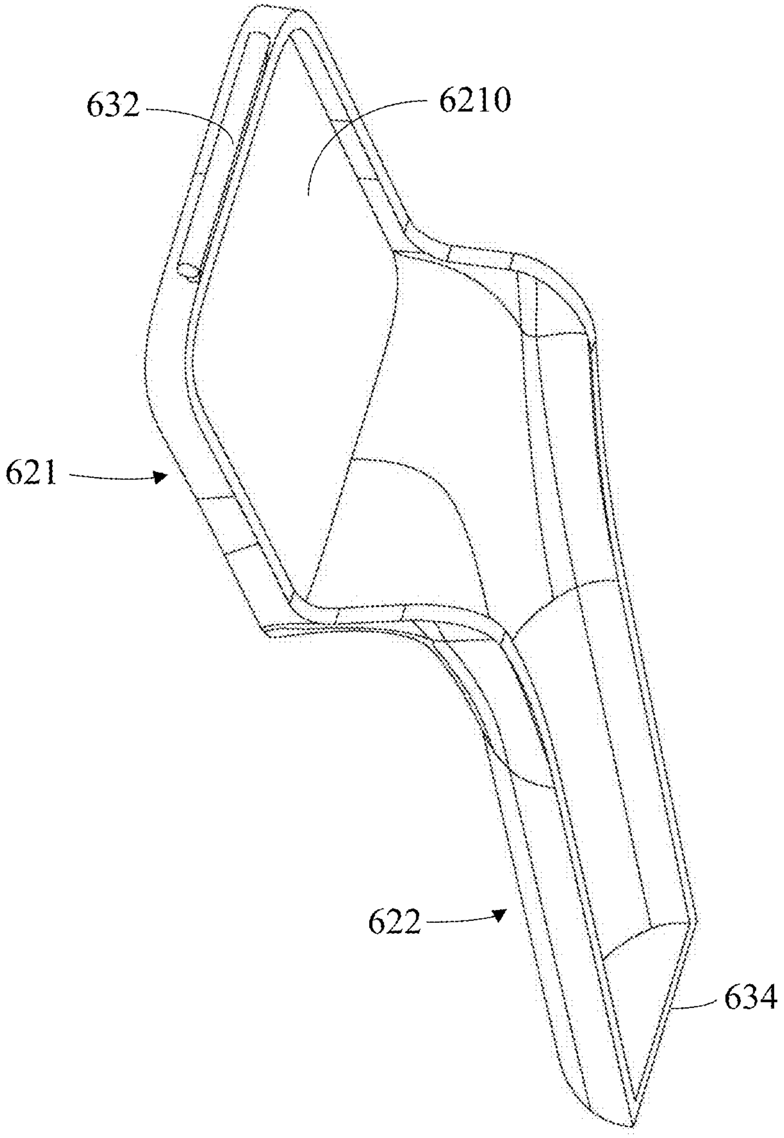
FIG. 4 is a schematic structural diagram of a second housing of a protective sleeve of a puncture device according to an embodiment of the present application.
Figure 5:
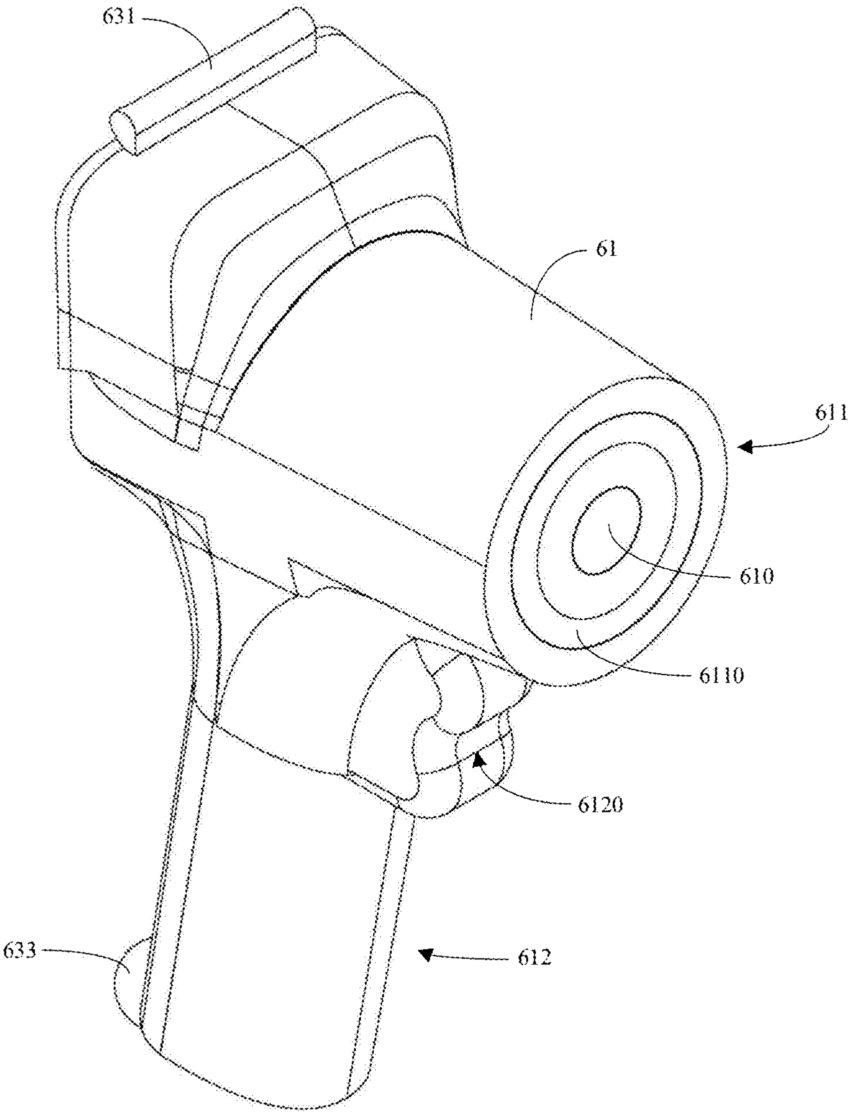
FIG. 5 is a schematic structural diagram of a first housing of a protective sleeve of a puncture device according to an embodiment of the present application.

In this embodiment, referring to FIGS. 3-5, the moving assembly is connected to the first housing 61 and the second housing 62; the first housing 61 and the second housing 62 are coaptated to form the accommodating cavity used for accommodating the puncture base 10 in the puncture device 1. Therefore, the interior of the accommodating cavity can be disinfected in advance, and the sterile environment may be created therein. Then, the puncture base 10 is disposed in a sterile protection environment, so that during the puncturing operation, the puncture base 10 is always in the sterile environment with less risk of polluting.

Optionally, the first housing 61 and the second housing 62 are made of materials, including, but not limited to a polymeric plastic material.

Optionally, the puncture base 10 contains an antimicrobial medium, which can inhibit growth of a colony on a product surface of a puncture base 10, or kill the colony.

Optionally, the accommodating cavity contains an antimicrobial medium which is provided in the accommodating cavity through a sponge or other carriers, so that the puncture base 10 can be better and more comprehensively protected sterilely.

Optionally, inner walls of the first housing 61 and the second housing 62 are rough, so as to prevent relative sliding between the protective sleeve 60 and the puncture base 10 from affecting the puncturing operation.

Optionally, a size of the mounting hole 610 may be set as needed; the mounting holes 610 in different sizes are disposed according to different types, and the protective sleeves 60 may be classified according to different mounting holes 610; and each type of the protective sleeve 60 corresponds to its adapted puncture device 1. A deformable mounting hole 610 may further be disposed, and the size of the mounting hole 610 may be changed directly on the protective sleeve 60 as actually needed without replacing the protective sleeve 60.

Optionally, the mounting hole 610 may be in a fixed size and adapted to all types of the puncture devices 1. The mounting hole 610 has a size equal to that in a maximum specification of the adapted puncture device 1, and thus there is no need to replace the protective sleeve 60.

It may be understood that during use of the puncture device 1, one end of the puncture base 10 close to the puncture assembly 40 needs to be connected to the puncture assembly 40, which is more prone to affecting the sterile environment for the puncture assembly 40. Therefore, in some possible implementations, the accommodating cavity is formed in the first housing 61.

Figure 2:
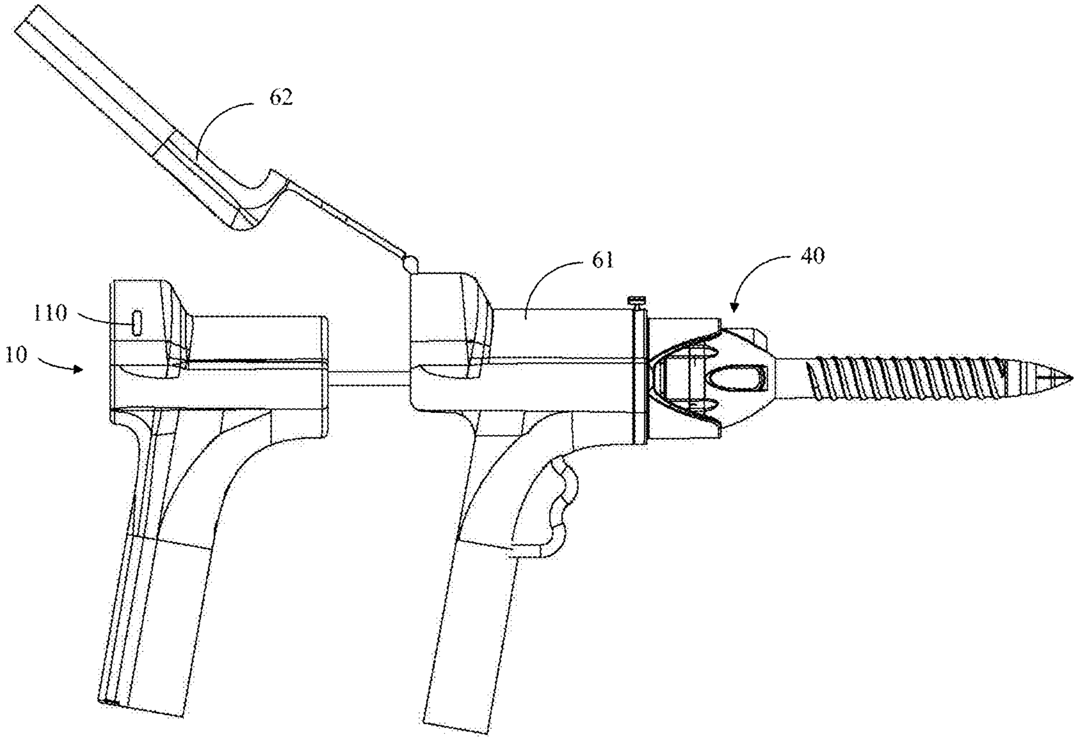
FIG. 2 is a schematic diagram of a positional relationship between a puncture base and a protective sleeve of a puncture device according to an embodiment of the present application.

In this embodiment, referring to FIG. 2, the first housing 61 is used for accommodating the puncture base 10 and closed by the second housing 62 which is corresponding to a protective cover, and thus the sterile accommodating cavity may be formed. The first housing 61 is provided with the mounting hole 610, which is conductive to assembly between the puncture base 10 and the puncture assembly 40 of the puncture device 1. The puncture base 10 is disposed in the sterile accommodating cavity, and when the puncture base 10 is assembled and connected with the puncture assembly 40, the sterile environment for the puncture assembly 40 during the surgery may not be destroyed. Further, after the puncture device 1 is used, it is only necessary to open the second housing 62 and take out the puncture base 10. Therefore, there is a less risk of polluting the puncture base 10 in the process of taking out the puncture base 10.

In this embodiment, referring to FIG. 5, since the puncture assembly 40 of the puncture base 10 needs to be in driving connection with the puncture base 10, by disposing the mounting hole 610 only in the first housing 61, the end of the puncture assembly 40 installed with the puncture base 10 is fully accommodated in the first housing 61. Thus, the puncture base 10 is in the sterile environment, and can be sterilely assembled with the puncture assembly 40. Also, the puncture base 10 can be reused, and chemically disinfection of the puncture base 10 is unnecessary, which reduces the risk of corrosion of the puncture base 10 by the disinfection agent, prolongs the service life of the puncture base 10, and lowers the medical cost.

It may be understood that in order to facilitate the puncturing operation, the puncture base 10 can have a handle to facilitate a handheld operation of the user. Therefore, in some possible implementations, the first housing 61 includes a first body portion 611 and a first handle portion 612. The second housing 62 includes a second body portion 621 and a second handle portion 622. A first accommodating cavity formed by coaptation of the first body portion 611 and the second body portion 621 is used for accommodating a puncture base body of the puncture device 1. The mounting hole 610 is formed in the first body portion 611. A second accommodating cavity formed by coaptation of the first handle portion 612 and the second handle portion 622 is used for accommodating the handle of the puncture device 1.

In this embodiment, referring to FIG. 3, according to structural features of the puncture base 10, a protective sleeve 60 suitable for the puncture base 10 with the handle is provided. As the puncture assembly 40 is partially connected to the puncture base body, the mounting hole 610 is formed in the first body portion 611 of the first housing 61.

Optionally, the first body portion 611 and the first handle portion 612 may be integrally formed, and the second body portion 621 and the second handle portion 622 may also be integrally formed.

Optionally, the first body portion 611 and the first handle portion 612 may be prepared separately, and then connected together through a bolt or in other ways. Similarly, the second body portion 621 and the second handle portion 622 may also be prepared separately, and then connected together through a bolt or in other ways.

Optionally, friction coefficients of surfaces of the first handle portion 612 and the second handle portion 622 are slightly large. That is, surfaces of the first handle portion 612 and the second handle portion 622 may be made relatively rough, which can prevent the puncturing operation from being affected by the handle being too slippery to hold when the user performs the puncturing operation.

Optionally, the surfaces of the first handle portion 612 and the second handle portion 622 may be provided with antiskid bulges.

Optionally, antiskid sleeves are sleeved on the surfaces of the first handle portion 612 and the second handle portion 622 respectively after the first handle portion 612 and the second handle portion 622 are coaptated, and then they can be sleeved on the handle portions of the protective sleeve 60 when in use, which is simple and convenient; and the antiskid sleeves may be mass produced.

As the mounting hole 610 is used for the tip 43 of the puncture assembly 40 to pass through to be in driving connection with the puncture base 10 in the protective sleeve 60, the puncture assembly 40 may rotate relative to the protective sleeve 60. Therefore, in some possible implementations, a friction coefficient of a peripheral surface of the mounting hole 610 is smaller than at least one of the friction coefficients of the surfaces of the first handle portion 612 and the second handle portion 622.

When the puncture assembly 40 rotates after the tip 43 of the puncture assembly 40 passes through the mounting hole 610, relative friction may be certainly generated between the side of the puncture assembly 40 having the tip 43 and the surface of the mounting hole 610. The stronger the friction is, the stronger resistance applied to the puncture base 10 driving the puncture assembly 40 is. In this embodiment, the friction coefficient of the peripheral surface of the mounting hole 610 is smaller, the resistance applied to the puncture base 10 driving the puncture assembly 40 is weaker, and the efficiency of the puncturing operation is higher. Meanwhile, the puncture base 10 does not need to use additional energy to drive the puncture assembly 40, which has the beneficial effect of energy conservation. However, as mentioned in the aforementioned embodiments, the friction coefficient at the handle needs to be increased to play an antiskid role. Therefore, the friction coefficient of the peripheral surface of the mounting hole 610 is smaller than that of the surface of the first handle portion 612 or the surface of the second handle portion 622. Alternatively, the friction coefficient of the peripheral surface of the mounting hole 610 is smaller than that of each of the surfaces of the first handle portion 612 and the second handle portion 622.

Optionally, the peripheral surface of the mounting hole 610 may be made of a relatively smooth or lubricated material, so as to reduce the friction force between the protective sleeve 60 and the side of the puncture assembly 40 having the tip 43.

Optionally, a smooth film may further be attached to one side of the protective sleeve 60 in contact with the puncture assembly 40.

Optionally, a lubricating medium may be coated on the side of the protective sleeve 60 in contact with the puncture assembly 40.

In some possible implementations, a groove 6110 is formed in one end of the first body portion 611 in contact with the puncture assembly 40. The mounting hole 610 is located in the groove 6110.

In this embodiment, after the tip 43 of the puncture assembly 40 passes through the mounting hole 610, due to the existence of the groove 6110, the side of the puncture assembly 40 having the tip 43 cannot completely contact with the side of the protective sleeve 60 having the mounting hole 610. Therefore, contact area between the protective sleeve 60 and the puncture assembly 40 becomes smaller, so that the side of the puncture assembly 40 having the tip 43 is less affected by the friction from the protective sleeve 60, and the puncture assembly 40 is easier to puncture. Due to the driving connection between the puncture assembly 40 and the puncture base 10, the low friction force between the puncture base 10 and the puncture assembly 40 also makes the puncture base 10 drive the puncture assembly 40 more efficient.

In this embodiment, the size of the groove 6110 is smaller than or equal to that of the side of the puncture assembly 40 having the tip 43, so as to prevent the side of the puncture assembly 40 having the tip 43 from falling in the groove 6110.

Optionally, the size of the groove 6110 is larger than that of the side of the puncture assembly 40 having the tip 43, so that the side of the puncture assembly 40 having the tip 43 may thoroughly embedded into the groove 6110, and connection between the puncture base 10 and the puncture assembly 40 can further become more stable. Then, a surface of the groove 6110 in contact with the end of the puncture assembly 40 having the tip 43 is made of a smooth material, or is coated with a lubricating fluid, etc., so as to weaken the friction force between the protective sleeve 60 and the puncture assembly 40.

In some possible implementations, the first handle portion 612 is provided with a key portion 6120 which is elastic. The key portion 6120 is used for being abutted against a key of the puncture device 1.

There may be electronic devices inside the existing puncture device 1, for example, the driving mechanism 13 driving the puncture assembly 40 to rotate, the camera 30 provided for conveniently photographing tissues at a tip of the puncture needle 42, etc. For convenience of use, keys for controlling the electronic devices may be disposed at the handle portion of the puncture base 10. In this embodiment, the first handle portion 612 is provided with an elastic key portion 6120. In a case that the protective sleeve 60 is sleeved on the puncture base 10, the user can control internal circuits in the whole puncture base 10 by pressing the elastic key portion 6120 and then pressing the key of the handle portion of the puncture base 10.

Optionally, a relatively hard key block is further provided on an inner wall of the key portion 6120. When the user presses the elastic key portion 6120, the key portion 6120 can be sunken inward. Meanwhile, a force applied by the user to the key portion 6120 is transmitted to the key on the puncture base 10 through the key block, so as to achieve an objective of pressing the key across the protective sleeve 60. After pressing, due to the elastic key portion 6120, the key portion 6120 can drive the key block to rebound to an initial state, and the key on the puncture base 10 cannot always be pressed.

The inventor of the present application has noted that a novel puncture device 1 is integrated with a display module 20 and a camera apparatus, which enables the user to view a specific situation of the tip of the puncture needle 42 at the tissues in the patient's body while the puncturing operation is performed. The display module 20 is disposed at the end of the puncture base 10 away from the puncture assembly 40. It may be understood that the display module 20 has built-in electronic device with a relatively high cost. If the display module 20 can be reused, the medical cost can be greatly saved.

Therefore, in some possible implementations, referring to FIG. 4, the second body portion 621 is provided with a transparent display region 6210. The display region 6210 is disposed opposite to the display module 20 of the puncture device 1.

In this embodiment, the second body portion 621 is disposed opposite to the end of the puncture base 10 away from the puncture assembly 40. The display module 20 of the puncture device 1 is also disposed at the end of the puncture base 10 away from the puncture assembly 40. Therefore, the second body portion 621 is provided with the transparent display region 6210, so that the users can view a content displayed by the display module 20 through the transparent display region 6210.

The display region 6210 may be disposed according to whether the adapted puncture device 1 has the display module 20, or a size and an orientation of the display module 20. If the puncture base 10 of the puncture device 1 is not provided with the display module 20, the second body portion 621 does not need to be provided with the transparent display region 6210. If the display module 20 of the puncture device 1 is arranged on a front surface of the puncture base 10 (i.e. a surface directly seen in FIG. 2), the transparent display region 6210 is disposed on a front surface of the first body portion 611 of the first housing 61.

In some possible implementations, the moving assembly includes a fixed frame 631 and a rotating shaft 632. Shaft holes are disposed opposite to each other in two ends of the fixed frame 631. The fixed frame 631 is disposed on a top of the first housing 61. The rotating shaft 632 is disposed on a top of the second housing 62. Two ends of the rotating shaft 632 are rotatably connected to the shaft holes oppositely disposed, respectively, in a matching manner.

In this embodiment, the first housing 61 and the second housing 62 can be rotatably connected in the matching manner through the fixed frame 631 and the rotating shaft 632. As there are enough spaces in the tops of the first housing 61 and the second housing 62, and the user does not need to touch the tops of the first housing 61 and the second housing 62 when holding the puncture base 10. Thus, the user's holding of the puncture base 10 may not be affected by the fixed frame 631 arranged on the top of the first housing 61 and the rotating shaft 632 arranged on the top of the second housing 62. During mounting, it is only necessary to open the second housing 62, put the puncture base 10 into the first housing 61, and then cover the second housing 62, which is simple and convenient to mount.

Optionally, the fixed frame 631 and the rotating shaft 632 may be positioned as actually needed. For example, the fixed frame 631 and the rotating shaft 632 may further be arranged on a side of the first housing 61 and a side of the second housing 62 respectively. The opening/closing between the first housing 61 and the second housing 62 is similar to a case of opening and closing a door.

Optionally, the first housing 61 and the second housing 62 may further be connected in other ways, for example, through a bolt. Alternatively, after coaptation of the first housing 61 and the second housing 62, the first housing 61 and the second housing 62 are fixed on their outer surfaces through a bandage.

Optionally, the rotating shaft 632 is disposed on the top of the first housing 61. The fixed frame 631 is arranged on the top of the second housing 62.

In some possible implementations, the moving assembly further includes a positioning member 633. A positioning groove 634 is formed in a bottom of the second housing 62 and the positioning member 633 is arranged at a bottom of the first housing 61. The positioning member 633 is inserted into the positioning groove 634.

In this embodiment, in order to make connection between the first housing 61 and the second housing 62 more stable, the moving assembly further includes the positioning member 633 arranged at the bottom of the first housing 61. In a case that the first housing 61 and the second housing 62 are coaptated, the positioning member 633 is inserted into the positioning groove 634 formed in the bottom of the second housing 62, so that better effects of fixing and limiting can be achieved.

Optionally, the bottoms of the first housing 61 and the second housing 62 are semi-circular, and a whole circle is formed after the bottoms of the first housing 61 and the second housing 62 are coaptated. The positioning member 633 may be semi-circular and has a size corresponding to the semi-circular bottom of the second housing 62. The positioning groove 634 is a semi-cylindrical space parallel to a plane where the bottom of the second housing 62 is located. After the positioning member 633 is inserted into the positioning groove 634, the bottoms of the first housing 61 and the second housing 62 are positioned, and thus relative movement therebetween may be avoided, and connection between the first housing 61 and the second housing 62 is more stable.

Optionally, a plurality of positioning members 633 may be arranged, and may be provided in the accommodating cavity, so as to fulfill the effect of supporting the puncture base 10 while performing positioning connection. A plurality of positioning grooves 634 may further be arranged correspondingly in which the positioning members 633 may be inserted to in the matching manner.

Optionally, the positioning members 633 and the positioning grooves 634 may be clamped or buckled with each other, and can be firmly fixed and easily dissembled.

In some possible implementations, a sealing strip 64 is arranged on one side of the first housing 61 contacting the second housing 62, and the first housing 61 is in sealing connection with the second housing 62 through the sealing strip 64.

In this embodiment, the first housing 61 is in sealing connection with the second housing 62 through the sealing strip 64, which can seal an environment in the whole accommodating cavity and prevent the colony that may be carried by the puncture base 10 during placement from spreading out of the accommodating cavity, and thus accommodating cavity may not be polluted by the external environment.

Optionally, the sealing strip 64 may further be arranged on one side of the second housing 62 contacting the first housing 61. Alternatively, the first housing 61 and the second housing 62 are both provided with the sealing strips 64.

Figure 7:
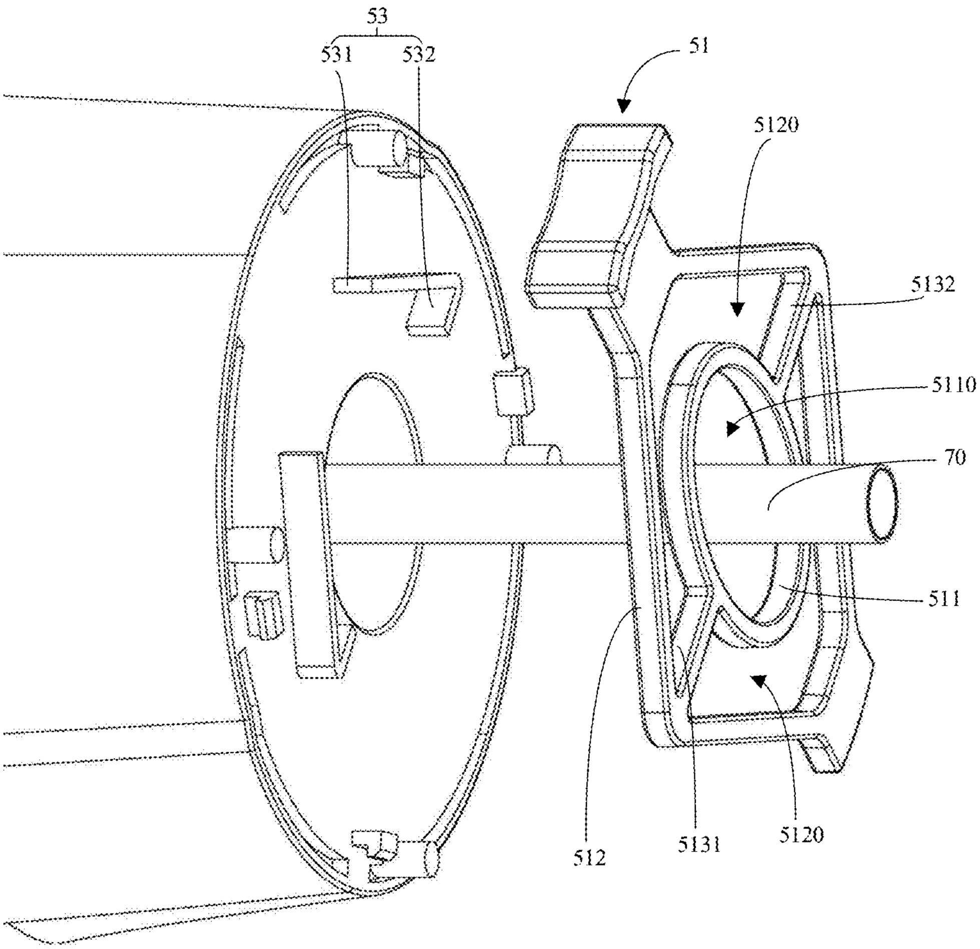
FIG. 7 is a partial enlarged view of a puncture device according to an embodiment of the present application.

In some possible implementations, referring to FIGS. 6 and 7, the disassembling/assembling assembly 50 includes an elastic buckle 51 connected to the protective sleeve 60. The elastic buckle 51 is provided with a deformation hole. The tip 43 of the puncture assembly 40 sequentially passes through the deformation hole and the mounting hole 610 to be in driving connection with the puncture base 10. If the elastic buckle 51 is in a state of not being subjected to an external force, a projection of the tip 43 on a plane where the deformation hole is located is partially overlapped with the deformation hole. If the elastic buckle 51 is in a state of being subjected to the external force, a projection of the tip 43 on the plane where the deformation hole is located falls within the deformation hole.

In this embodiment, the disassembling/assembling assembly 50 of the puncture device 1 is provided with the elastic buckle 51. The puncture assembly 40 passes through the deformation hole of the elastic buckle 51 and the mounting hole 610 of the protective sleeve 60 to be connected to the puncture base 10. The deformation hole of the elastic buckle 51 can be changed in size or shape when being subjected to the external force. The size of the deformation hole is inconsistent with that of the tip 43 of the puncture assembly 40 when the elastic buckle 51 is not subjected to the external force, and the tip 43 cannot pass through the deformation hole. If the elastic buckle 51 is subjected to the external force, the deformation hole can deform to a suitable size, so that the tip 43 passes through the deformation hole and the mounting hole 610 of the protective sleeve 60 to be connected to the puncture base 10. Quick disassembly/assembly between the puncture base 10 and the puncture assembly 40 can be achieved through the above disassembling/assembling assembly 50, which improves the efficiency of the puncturing operation, and enables the puncture base 10 to be reused to save the medical cost. The puncture assemblies 40 in different sizes can also be connected to the puncture bases 10 in different sizes through the above disassembling/assembling assembly 50, which improves the compatibility of the surgery, and makes application scenarios wide.

Figure 15:
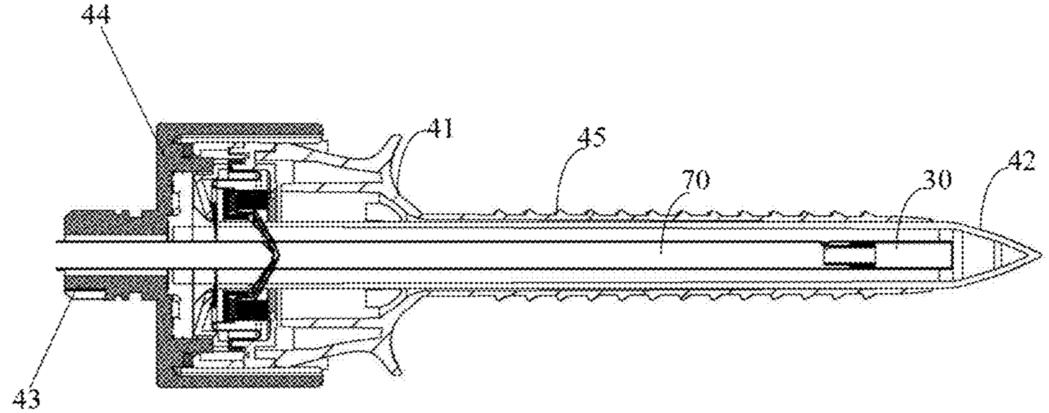
FIG. 15 is a sectional view of a puncture assembly according to an embodiment of the present application.

Optionally, referring to FIG. 15, the puncture device 1 further includes an adjusting rod 70 including an end located in the puncture base 10 and another end extending into the puncture assembly 40 and connected to the camera 30 in the puncture assembly 40. The camera 30 may photograph tissues in a body during the puncturing operation, so that the doctor can observe an environment of the tissues in the body while performing the operation, so as to avoid an unnecessary wound caused by puncturing to the tissues in the patient.

In some possible implementations, referring to FIG. 7, the elastic buckle 51 includes a first deformation structure 511, a second deformation structure 512 and connecting structures 513 connecting the first deformation structure 511 and the second deformation structure 512.

The first deformation structure 511 is provided with a first through hole 5110 which forms the deformation hole.

The second deformation structure 512 is provided with a second through hole 5120.

A projection of the first deformation structure 511 on a plane where the second deformation structure 512 is located is in the second through hole 5120.

In this embodiment, the first deformation structure 511 and the second deformation structure 512 of the elastic buckle 51 are hollowed in the middle. A size of the first deformation structure 511 is smaller than that of the second deformation structure 512, and the first deformation structure 511 is disposed in the second through hole 5120 of the second deformation structure 512. As the first deformation structure 511 and the second deformation structure 512 are both of a hollowed structure and are not contacted with each other, the connecting structures 513 are used for connecting the first deformation structure 511 and the second deformation structure 512 respectively, so that the first deformation structure 511 and the second deformation structure 512 are in a relatively stable connection state. If the second deformation structure 512 is subjected to the external force, the first deformation structure 511 can also be subjected to the external force transmitted by the connecting structures 513, and thus deforms. The first through hole 5110 can also deform and form the deformation hole for the tip 43 of the puncture assembly 40 conveniently passing through.

In some possible implementations, the connecting structures 513 include a first connecting structure 5131 and a second connecting structure 5132 opposite to each other.

If the elastic buckle 51 is in the state of not being subjected to the external force, the deformation hole is elliptical, projections of the first connecting structure 5131 and the second connecting structure 5132 on the plane where the deformation hole is located respectively form angles $\alpha$ with a straight line where a short axis of the deformation hole is located, where $0 \leq \alpha < 45°$.

In this embodiment, the first connecting structure 5131 and the second connecting structure 5132 are disposed opposite to each other. When the elastic buckle 51 is in a relaxed state and not subjected to the external force, the first through hole 5110 is elliptical. It may be understood that the elliptical hole is different from a circular hole. The elliptical first through hole 5110 has a long axis and a short axis. Assuming that the tip 43 of the puncture assembly 40 is cylindrical, and a diameter of a cross section of the tip 43 is larger than that of the short axis of the elliptical deformation hole, the tip 43 cannot passes the deformation hole. When the elastic buckle 51 is in the state of being subjected to the external force, for example, the elastic buckle 51 is compressed, so that the long axis of the elliptical first through hole 5110 is compressed and shortened, and the short axis thereof becomes long, and the elliptical first through hole 5110 deforms into a nearly-circular deformation hole. When the short axis of the deformation hole is increased to be larger than that of the cross section at the tip 43, the tip 43 may pass through the deformation hole. For another example, the elastic buckle 51 is stretched, so that the short axis of the elliptical first through hole 5110 elongated and the long axis thereof is shortened, so that the elliptical first through hole 5110 deforms into the nearly-circular deformation hole. If the short axis of the deformation hole is increased to be larger than that of the cross section at the tip 43, and the short axis is still smaller than the long axis, the tip 43 may pass through the deformation hole. The elastic buckle 51 is such arranged that the tip 43 can quickly pass through or be removed from the puncture base 10. During use, after the external force applied to the elastic buckle 51 disappears, the deformation hole returns to the initial state again and locks the tip 43 or the tip 43 and the connecting cover 44, which may ensure that the puncture assembly 40 may not be separated from the puncture base 10 and is convenient and efficient to use.

In this embodiment, a connecting line between the first connecting structure 5131 and the second connecting structure 5132 forms an angle $\alpha$ with the straight line where the short axis of the deformation hole is located. That is, the first connecting structure 5131 and the second connecting structure 5132 are approximately coincident with the short axis of the deformation hole or have a small deflection angle with the short axis; and it is only necessary to make the short axis longer during deformation.

The first connecting structure 5131 and the second connecting structure 5132 are both elongated, and disposed in the straight line where the short axis of the deformation hole is located.

It may be understood that the essence of deformation of the first through hole 5110 is that the first connecting structure 5131 and the second connecting structure 5132 are stretched toward both ends of the short axis of the ellipse at the same time, which drives a length of the short axis of the ellipse to change. When the first connecting structure 5131 and the second connecting structure 5132 are both disposed in the straight line where the short axis of the deformation hole is located, the first connecting structure 5131 and the second connecting structure 5132 are directly in a state of being stretched toward both ends of the short axis, and then the short axis may deform to the size matching with that of the tip 43. Such arrangement can make the deformation process of the elastic buckle 51 more labor-saving.

Optionally, a clamping groove is formed in the end of the tip 43 away from the puncture base 10. After the puncture assembly 40 passes through the deformation hole, a frame of the deformation hole may be clamped in the clamping groove, which can make connection of the puncture assembly 40 and the puncture base 10 more stable.

Optionally, referring to FIGS. 6 and 7, the elastic buckle 51 further includes a fixed cover 52, a first handle 514 and a supporting portion 515, where the first handle 514 and the supporting portion 515 are disposed opposite to each other.

The first handle 514 and the supporting portion 515 are each connected to the second deformation structure 512.

The fixed cover 52 is provided with a third through hole 520 corresponding to the deformation hole, and forms an accommodating region with one side of the puncture base 10 close to the elastic buckle 51. The elastic buckle 51 is disposed in the accommodating region.

A first opening 521 is formed in a peripheral of the fixed cover 52. The first handle 514 passes through the first opening 521, so as to extend out of the accommodating region. An end of the supporting portion 515 away from the second deformation structure 512 is abutted against an inner side wall of the fixed cover 52.

In this embodiment, the first opening 521 is formed in the peripheral of the fixed cover 52. The first handle 514 passes through the first opening 521, so as to extend out of the accommodating region. The supporting portion 515 is abutted against an inner wall of the fixed cover 52. The supporting portion 515 opposite to the first handle 514 can be driven by pressing the first handle 514 to extrude the inner wall of the fixed cover 52, so that the deformations of the first deformation structure 511 and the second deformation structure 512 may be achieved.

Figure 8:
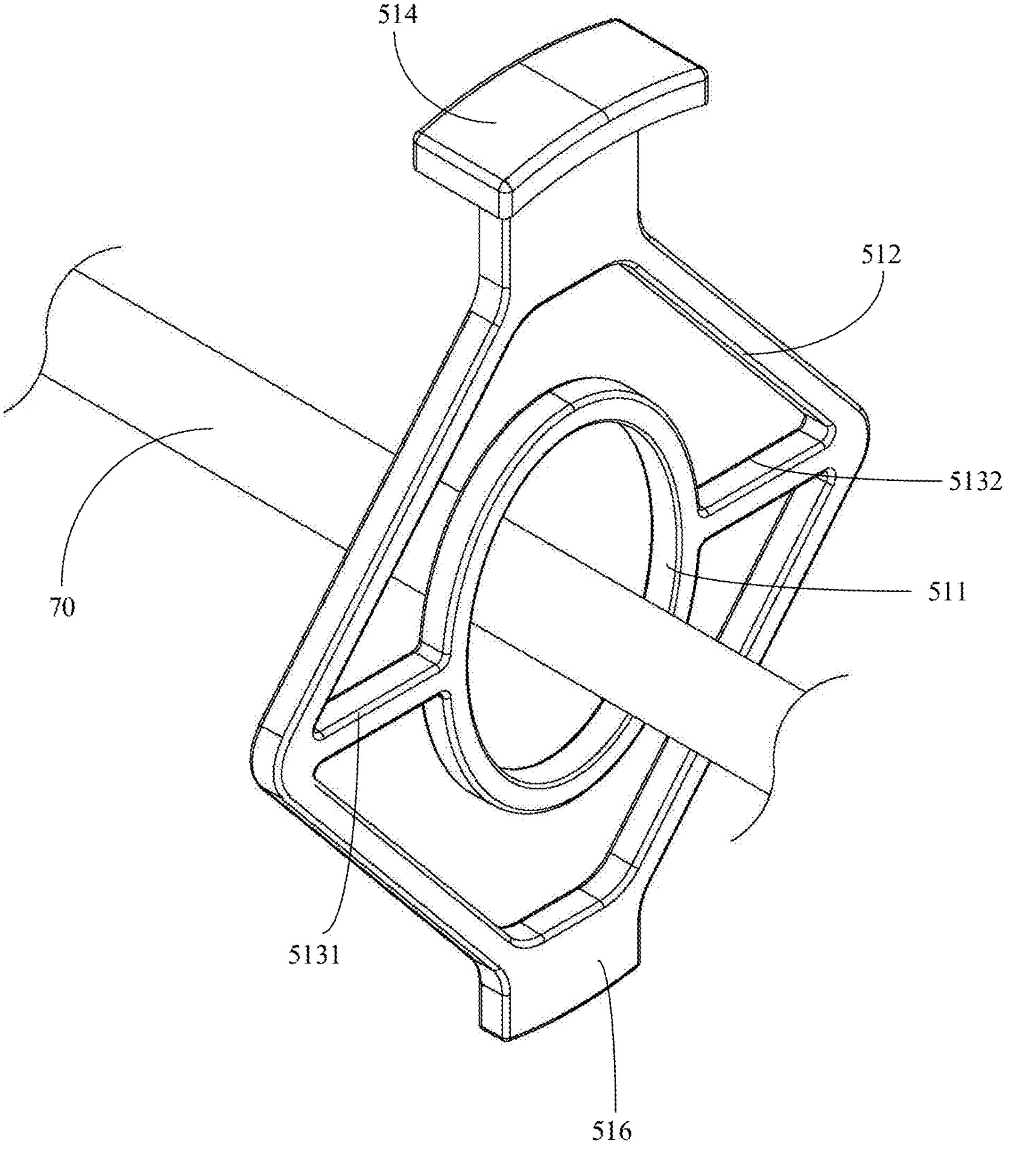
FIG. 8 is a schematic structural diagram of an elastic buckle of a puncture device according to an embodiment of the present application.

In some possible implementations, referring to FIG. 8, the elastic buckle 51 further includes the first handle 514 and a second handle 516 disposed opposite to each other.

The first handle 514 and the second handle 516 are each connected to the second deformation structure 512.

When the elastic buckle 51 is in the state of not being subjected to the external force, projections of the first handle 514 and the second handle 516 on the plane where the deformation hole is located respectively form angles β with a straight line where the long axis of the deformation hole is located, where 0≤β<45°.

In this embodiment, the user applies the external force to the first handle 514 and the second handle 516. When the elastic buckle 51 is in the state of not being subjected to the external force, the projections of the first handle 514 and the second handle 516 on the plane where the deformation hole is located respectively form the angles β with the straight line where the long axis of the deformation hole is located, where 0≤β<45° (that is, the first handle 514 and the second handle 516 are approximately coincident with the short axis of the deformation hole or have a small deflection angle with the short axis). In the case that the first connecting structure 5131 and the second connecting structure 5132 form the angles α with the short axis of the deformation hole (that is, the first connecting structure 5131 and the second connecting structure 5132 are approximately coincident with the short axis of the deformation hole or have a small deflection angle with the short axis), the deformations of the first deformation structure 511 and the second deformation structure 512 may be achieved by pressing the first handle 514 and the second handle 516 disposed oppositely, so that the short axis becomes longer. In the case that the first connecting structure 5131 and the second connecting structure 5132 form the angles α with the long axis of the deformation hole, the deformations of the first deformation structure 511 and the second deformation structure 512 may be achieved by stretching the first handle 514 and the second handle 516 disposed oppositely, so that the short axis becomes longer.

Optionally, when the elastic buckle 51 is in the state of not being subjected to the external force, the projections of the first handle 514 and the second handle 516 on the plane where the deformation hole is located respectively form the angles β with the straight line where the short axis of the deformation hole is located, where 0≤β<45°.

When the elastic buckle 51 is in the state of not being subjected to the external force, the projections of the first handle 514 and the second handle 516 on the plane where the deformation hole is located respectively form the angles β with the straight line where the short axis of the deformation hole is located, where 0≤β<45°. In the case that the first connecting structure 5131 and the second connecting structure 5132 form the angles α with the long axis of the deformation hole, the deformations of the first deformation structure 511 and the second deformation structure 512 may be achieved by stretching the first handle 514 and the second handle 516 disposed oppositely, so that the short axis becomes longer.

Optionally, the first deformation structure 511 is an elliptical ring, the second deformation structure 512 is a rhombic frame, and the first connecting structure 5131 and the second connecting structure 5132 are both elongated. The first connecting structure 5131 and the second connecting structure 5132 are disposed oppositely in the straight line where the short axis of the elliptical first deformation structure 511 is located, and are connected to two opposite corners of an outer wall of the first deformation structure 511 and an inner wall of the second deformation structure 512. The first handle 514 and the second handle 516 are both disposed in the straight line where the long axis of the elliptical first deformation structure 511 is located, and located at two opposite corners of the second deformation structure 512. The distance between two corners of the second deformation structure 512 respectively connected to the first connecting structure 5131 and the second connecting structure 5132 becomes longer by relatively pressing the first handle 514 and the second handle 516. Therefore, the first connecting structure 5131 and the second connecting structure 5132 drive the deformations of the deformation structure 511. That is, the short axis of the first deformation structure 511 can be stretched and becomes longer, and an ellipse can change to a positive circle, so that the tip 43 can pass through the first deformation structure 511. In this embodiment, the second handle 516 disposed opposite to the first handle 514 may further be replaced with the supporting portion 515.

In some possible implementations, the connecting structures 513 include the first connecting structure 5131 and the second connecting structure 5132 disposed opposite to each other.

When the elastic buckle 51 is in the state of not being subjected to the external force, the deformation hole is elliptical, the projections of the first connecting structure 5131 and the second connecting structure 5132 on the plane where the deformation hole is located respectively form the angles α with the straight line where the long axis of the deformation hole is located, where 0≤α<45°.

In this embodiment, the projections of the first connecting structure 5131 and the second connecting structure 5132 on the plane where the deformation hole is located respectively form the angles α with the straight line where the long axis of the deformation hole is located, where 0≤α<45°. Then, by applying the external force to the elastic buckle 51, the long axis becomes shorter and the short axis becomes longer, and then the tip 43 of the puncture assembly 40 can pass through the deformation hole.

In some possible implementations, the elastic buckle 51 further includes the first handle 514 and a second handle 516 disposed opposite to each other.

The first handle 514 and the second handle 516 are each connected to the second deformation structure 512.

When the elastic buckle 51 is in the state of not being subjected to the external force, projections of the first handle 514 and the second handle 516 on the plane where the deformation hole is located respectively form the angles β with a straight line where the long axis of the deformation hole is located, where 0≤β<45°.

In this embodiment, when the elastic buckle 51 is in the state of not being subjected to the external force, the projections of the first handle 514 and the second handle 516 on the plane where the deformation hole is located respectively form the angles β with the straight line where the long axis of the deformation hole is located, where 0≤β<45°. In the case that the first connecting structure 5131 and the second connecting structure 5132 respectively form the angles α with the long axis of the deformation hole, the deformations of the first deformation structure 511 and the second deformation structure 512 may be achieved by pressing the first handle 514 and the second handle 516 disposed oppositely, so that the short axis becomes longer. In the case that the first connecting structure 5131 and the second connecting structure 5132 respectively form the angles α with the short axis of the deformation hole, the deformations of the first deformation structure 511 and the second deformation structure 512 may be achieved by stretching the first handle 514 and the second handle 516 disposed oppositely, so that the short axis becomes longer.

Optionally, when the elastic buckle 51 is in the state of not being subjected to the external force, the projections of the first handle 514 and the second handle 516 on the plane where the deformation hole is located respectively form the angles β with the straight line where the short axis of the deformation hole is located, where 0≤β<45°.

When the elastic buckle 51 is in the state of not being subjected to the external force, the projections of the first handle 514 and the second handle 516 on the plane where the short axis of the deformation hole is located respectively form the angles β with the straight line where the short axis of the deformation hole is located, where 0≤β<45°. In the case that the first connecting structure 5131 and the second connecting structure 5132 respectively form the angles α with the short axis of the deformation hole, the deformations of the first deformation structure 511 and the second deformation structure 512 may be achieved by stretching the first handle 514 and the second handle 516 disposed oppositely, so that the short axis becomes longer.

Referring to FIG. 6, the disassembling/assembling assembly 50 further includes the fixed cover 52. The fixed cover 52 forms an accommodating region with the side of the puncture base 10 close to the elastic buckle 51, and the elastic buckle 51 is disposed in the accommodating region. The fixed cover 52 is provided with the third through hole 520 corresponding to the deformation hole.

In this embodiment, the elastic buckle 51 is fixed to the protective sleeve 60 by the fixed cover 52. If there is a need for replacing the puncture assembly 40, the puncture assembly 40 is disassembled through the whole disassembling/assembling assembly 50, and the remaining puncture base 10 and disassembling/assembling assembly 50 may be reused. As being less polluted, the puncture base 10 and the disassembling/assembling assembly 50 are easy to disinfect.

Mutually matched clamping key structures are provided on one side of the protective sleeve 60 close to the elastic buckle 51 and one side of the fixed cover 52 close to the elastic buckle 51, and the fixed cover 52 is fixed with the protective sleeve 60 through the clamping key structures.

Optionally, the first opening 521 and a second opening (not shown in the drawing) is formed in the peripheral of the fixed cover 52. The first handle 514 passes through the first opening 521 to extend out of the accommodating region; and the second handle 516 passes through the second opening to extend out of the accommodating region.

In this embodiment, since the first handle 514 and the second handle 516 need to be pressed or stretched by the user, they need to be disposed outside the fixed cover 52. In this embodiment, since the first opening 521 and the second opening are formed in the peripheral of the fixed cover 52, after the fixed cover 52 is fixed with the puncture base 10, the first opening 521 and the second opening may be sealed. Then, the first handle 514 and the second handle 516 of the elastic buckle 51 extend outside without exposing the first opening 521 and the second opening.

Optionally, two holes may also be directly provided in the peripheral of the fixed cover 52, the first handle 514 and the second handle 516 extend out of the holes and connect with two pressing portions. Sizes of the pressing portions are larger than those of the holes formed in the peripheral of the fixed cover 52. Therefore, there is no need to worry about the first handle 514 and the second handle 516 falling into the accommodating region.

It will be understood that when the external force applied to the elastic buckle 51 is strong enough, the elastic buckle 51 may excessively deform. For example, the original long axis of the elliptical first through hole 5110 is excessively compressed and becomes an actual short axis, and the original short axis is excessively stretched and becomes an actual long axis. At this time, the original long axis is even shorter than the diameter of the cross section of the tip 43 of the puncture assembly 40, which causes the tip 43 of the puncture assembly 40 cannot pass through or may be separated from the deformation hole. As the elastic buckle 51 is located in the fixed cover 52, it is difficult for the user to observe deformation of the elastic buckle 51.

Therefore, in some possible implementations, the disassembling/assembling assembly 50 further includes the limiting member 53.

The limiting member 53 is fixedly connected to the side of the fixed cover 52 close to the elastic buckle 51. The limiting member 53 is disposed in the second through hole 5120. The limiting member 53 is used for limiting at least one of the first deformation structure 511, the second deformation structure 512, the first connecting structure 5131 and the second connecting structure 5132, when the elastic buckle 51 is deformed.

In this embodiment, the elastic buckle 51 may be limited by the limiting member 53 disposed on one side of the fixed cover 52. The limiting member 53 is disposed on one side of the fixed cover 52, the limiting member 53 is clamped into the second through hole 5120 to limit excessive deformation of the elastic buckle 51, which ensures that the tip 43 of the puncture assembly 40 can pass through the deformation hole.

Optionally, the limiting member 53 is fixedly connected to one side of the protective sleeve 60 close to the elastic buckle 51. The limiting member 53 is disposed in the second through hole 5120. The limiting member 53 is used for limiting at least one of the first deformation structure 511, the second deformation structure 512, the first connecting structure 5131 and the second connecting structure 5132, when the elastic buckle 51 is deformed.

The limiting member 53 may further be disposed on the side of the protective sleeve 60 contacting the elastic buckle 51, as long as the limiting member 53 can be clamped into the second through hole 5120 and limit excessive deformation of the elastic buckle 51.

Optionally, the limiting member 53 may be provided as one. Alternatively, the limiting members 53 may be provided as plural, which has better effect. Optionally, the limiting member 53 may be a separate individual, and may be directly connected to the protective sleeve 60 or the fixed cover 52 through adhesion or in other connection ways when being used. Optionally, the limiting member 53 includes a first limiting block 531 and a second limiting block 532 which are mutually connected and form an angle therebetween. The first limiting block 531 is used for limiting at least one of the first deformation structure 511 and the second deformation structure 512, when the elastic buckle 51 is deformed. The second limiting block 532 is used for limiting at least one of the first connecting structure 5131 and the second connecting structure 5132, when the elastic buckle 51 is deformed.

It may be understood that one or more sealed space regions may be formed among the outer wall of the first deformation structure 511 (i.e. the side of the first deformation structure 511 close to the second deformation structure 512), the first connecting structure 5131, the second connecting structure 5132 and the inner wall of the second deformation structure 512 (i.e. the side of the second deformation structure 512 close to the first deformation structure 511). A certain angle is formed between the first connecting structure 5131 and the outer wall of the first deformation structure 511. When the external force is applied to the elastic buckle 51, the angle may change. The first limiting block 531 and the second limiting block 532 which are mutually connected and form the angle therebetween can be used for limiting an excessive change of the angle, and then the effect of indirectly limiting excessive deformation of the elastic buckle 51 may be achieved. Similarly, certain angles are formed between the first connecting structure 5131 and the inner wall of second deformation structure 512, between the second connecting structure 5132 and the outer wall of the first deformation structure 511, and between the second connecting structure 5132 and the inner wall of second deformation structure 512, respectively. When the external force is applied to the elastic buckle 51, the angles may change. The first limiting block 531 and the second limiting block 532 which are mutually connected and form the angle therebetween can be used for limiting excessive changes of the angles, and then the effect of limiting excessive deformation of the elastic buckle 51 may be achieved.

It may be understood that when using the puncture device 1, the user needs to control his/her own strength, speed, etc., and if the user takes a lot of effort to perform the puncturing operation, it may affect other later surgical operations. And, when the user rotates the puncture assembly 40 in a reciprocating manner cyclically, the needle tip of the puncture needle 42 of the puncture assembly 40 may cause a certain damage on the tissues in the patient's body. Therefore, in some possible implementations, referring to FIG. 9, the puncture base 10 includes a housing 11 and a driving mechanism 13.

The driving mechanism 13 is disposed in the housing 11. The tip 43 of the puncture assembly 40 is in driving connection with the driving mechanism 13.

In this embodiment, the driving mechanism 13 is fixed in the housing 11. The tip 43 of the puncture assembly 40 passes through the deformation hole of the disassembling/assembling assembly 50 and the mounting hole 610 of the protective sleeve 60, and then is connected to the driving mechanism 13 in the housing 11. The driving mechanism 13 provides a power for rotation of the puncture assembly 40, and the user can push the puncture device 1 into the tissues only needs to use a very weak force. Meanwhile, an unnecessary damage to the tissues in the patient's body caused by the puncture needle 42 being affected by the user is avoided.

Optionally, the driving mechanism 13 includes a driving motor 131 and a driving gear 132. The driving gear 132 is fixedly connected to an output end of the driving motor 131. A gear-tooth structure is provided on a circumferential direction of the tip 43 of the puncture assembly 40. The driving gear 132 is engaged with the gear-tooth structure.

In this embodiment, the driving gear 132 connected to the driving motor 131 is driven by the driving motor 131 to rotate, which in turn drives the tip 43 of the puncture assembly 40 to rotate. The driving motor 131 only needs to occupy a very small space to realize a driving function, and the driving motor 131 is small and convenient, and is available in materials. The gear-tooth structure is arranged on the circumferential direction of the tip 43 of the puncture assembly 40, so that the tip 43 of the puncture assembly 40 becomes a traditional driven gear, which simplifies a specific structure of the puncture assembly 40 without an additional driven gear; and the idea is ingenious.

The driving motor 131 is disposed in the housing 11 of the puncture base 10, and may be reused. Optionally, the housing 11 is further provided with a key by which the driving mechanism 13 may be controlled to drive the puncture assembly 40 to rotate.

Figure 13:
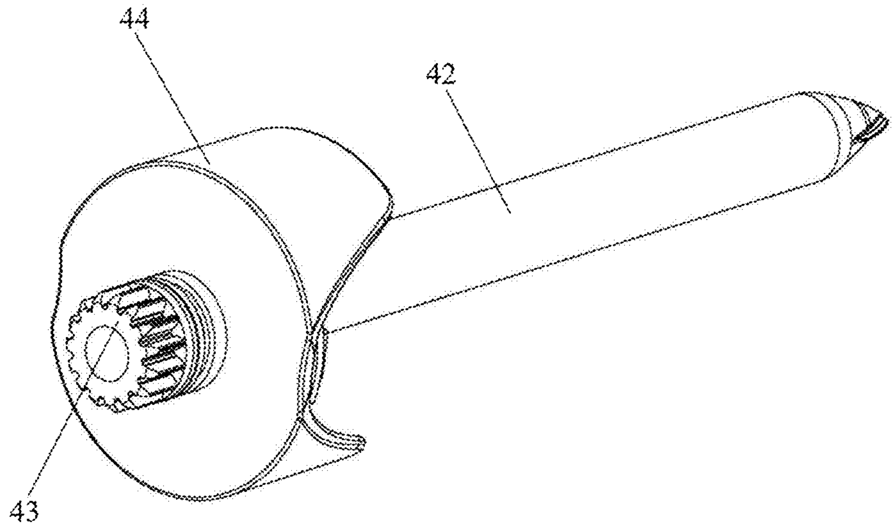
FIG. 13 is a schematic diagram of a positional relationship among a puncture needle, a connecting cover and a tip of a puncture device according to an embodiment of the present application.
Figure 14:
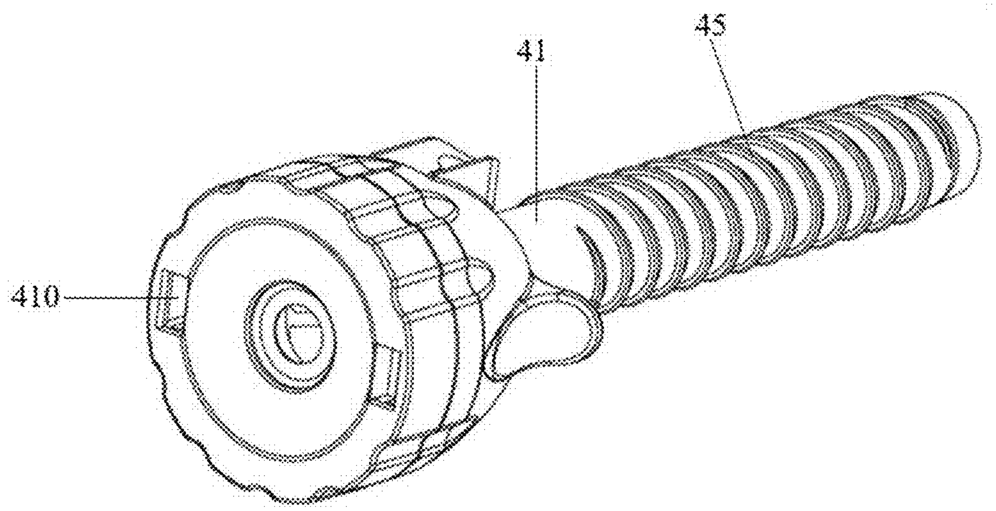
FIG. 14 is a schematic structural diagram of a puncture sheath with a thread structure according to an embodiment of the present application.

In some possible implementations, referring to FIGS. 13 and 14, the puncture assembly 40 includes a connecting cover 44, a puncture needle 42 and a puncture sheath 41.

The puncture sheath 41 is sleeved outside the puncture needle 42.

A needle head end of the puncture needle 42 extends out of a sheath head end of the puncture sheath 41, and a needle tail end of the puncture needle 42 and the tip 43 are coaxial and fixedly connected to both sides of the connecting cover 44, respectively.

The connecting cover 44 is in driving connection with the sheath tail end of the puncture sheath 41.

In this implementation, the tip 43 is fixedly connected to one side of the connecting cover 44, and the needle tail end of the puncture needle 42 is fixedly connected to the other side of the connecting cover 44. Therefore, the driving motor 131 drives the tip 43 to rotate, which makes the puncture needle 42 rotate, so as to perform puncturing. However, the puncture sheath 41 is sleeved outside the puncture needle 42, the connecting cover 44 is in driving connection with the sheath tail end of the puncture sheath 41. Rotation of the puncture needle 42 can drive rotation of the puncture sheath 41, that is, only one driving motor 131 is needed to drive rotations of the puncture needle 42 and the puncture sheath 41. The puncture needle 42 and the puncture sheath 41 both penetrate into the tissues in the patient's body, and the puncture needle 42 is taken out. The driving connection between the puncture needle 42 and the puncture sheath 41 is disconnected, leaving the puncture sheath 41 for a next surgical operation.

In some possible implementations, the connecting cover 44 includes a connecting plate, an extension sleeve and a clamping key. Both sides of the connecting plate are fixedly connected to the needle tail end of the puncture needle 42 and the tip 43 respectively. The extension sleeve and the clamping key are fixedly connected to one side of the connecting plate facing the puncture sheath 41, separately. The extension sleeve is sleeved outside the sheath tail end of the puncture sheath 41. A clamping groove 410 matched with the clamping key is disposed in one side of the sheath tail end of the puncture sheath 41 facing the connecting plate.

In this embodiment, the connecting plate is connected to connect the tip 43 and the puncture needle 42, the extension sleeve is fixedly connected to the connecting plate and covers the sheath tail end of the puncture sheath 41. Meanwhile, the clamping key is in clamping connection with the clamping groove 410 of the sheath tail end in the matching manner, thereby achieving driving connection between the puncture needle 42 and the puncture sheath 41. The extension sleeve and the connecting plate jointly form a shape similar to a cover, to cover the sheath tail end of the puncture sheath 41. The space in the cover is reasonably used, and the clamping key is arranged in the cover, which may achieve an objective of driving connection, and may further wrap the sheath tail end, the clamping key and the clamping groove 410, to isolate a clamping part from the external environment. The puncture sheath 41 and the puncture needle 42 are reasonably integrated as a whole, which is convenient to take and use.

Optionally, referring to FIG. 14, a thread structure 45 is provided on an outer wall of the puncture sheath 41. A head end of the thread structure 45 is close to the sheath head end of the puncture sheath 41, and a tail end of the thread structure 45 is close to the sheath tail end of the puncture sheath 41. As the puncture sheath 41 is in driving connection with the puncture needle 42 through the connecting cover 44, the driving motor 131 drives the connecting cover 44 to rotate, and then the connecting cover 44 drives the puncture sheath 41 to rotate into the tissues in the patient's body. However, torsional extrusion type laparotomy or vertical-pressure laparotomy of the traditional puncture device 1 is changed into continuous spiral puncture type laparotomy through the puncture sheath 41 with a one-way thread structure 45. Under the effect of driving rotation provided by the driving motor 131, it is easier to puncture into the patient's body, and the efficiency of the punctured operation is improved. Also, the thread structure 45 is embedded into the tissues in the body during puncturing, which makes the puncture sheath more stable relative to the tissues in the body, reduces the risk of the puncture sheath 41 sliding relative to the body tissues in the body, and facilitates the later surgical operation in the puncture sheath.

Optionally, the thread structure 45 is disposed on the outer wall of the puncture sheath 41, and it may be a continuous thread structure, or may be a thread structure including various thread segments distributed on a spiral trajectory.

Most of the puncture devices in the prior art do not have their own optical endoscopic camera function, and the doctor cannot observe the tissues in the wound while puncturing. Some visual puncture devices are connected to imaging systems through external cables. When using such visual puncture devices, the doctor needs to observe an audio-visual system placed on an edge of an operating table while holding the puncture device for the puncturing operation, which makes it easy to feel tired.

Therefore, the present application further provides an embodiment, in which the puncture device 1 further includes a display module 20 and a camera 30. The display module 20 is disposed at the end of the puncture base 10 away from the puncture assembly 40, the camera 30 is disposed at the end of the puncture assembly 40 away from the puncture base 10, and the camera 30 is in communication connection with the display module 20.

In this embodiment, the display module 20 and the puncture assembly 40 are disposed at both ends of the puncture base 10 respectively, and the display module 20 is integrated into the puncture base 10 itself, so that the doctor can directly observe the internal tissue environment through the display module 20 arranged on the puncture base 10 while using the puncture device 1 for puncturing.

Optionally, the driving motor 131 and the display module 20 are both disposed in the housing 11.

In this embodiment, the driving motor 131 and the display module 20 are both disposed in the housing 11, the display module 20 is disposed at one end in the housing 11, and the driving motor 131 is laterally disposed on one side of the display module 20. Space in the housing 11 is reasonably used according to functions of various components, and the display module 20 and the driving motor 131 are integrated into the housing 11 to be fixed, so that the housing 11 as well as the driving motor 131 and the display module 20 in the housing 11 are all effectively protected and may be reused. Optionally, the display module 20 is located at one end of the puncture base 10 away from the puncture assembly 40 in the housing 11, and is connected to the housing 11. The display module 20 and the puncture assembly 40 are located at two opposite ends of the housing 11 respectively.

Optionally, a projection of the driving motor 131 on a plane where the display module 20 is located falls within the display module 20.

In this embodiment, positions of the driving motor 131 and the display module 20 in the puncture base 10 may be reasonably designed according to structural features thereof. The driving motor 131 is disposed between the display module 20 and the puncture assembly 40, and an axial direction of the driving motor 131 is parallel to that of the puncture assembly 40. Such design makes the puncture base 10 exquisite in structure and reasonable in profiling.

Optionally, in the housing 11 of the puncture base 10, the display module 20 and the puncture assembly 40 are disposed at the two opposite ends of the puncture base 10 respectively, the display module 20 is connected to the housing 11, and the display module 20 and the puncture assembly 40 are located at the two opposite ends of the housing 11 respectively. Therefore, the space in the housing 11 is reasonably used. Meanwhile, the user observes the specific environment for the tissues in the body through the display screen 23 while puncturing. The camera 30 is signally connected to the display module 20, and the camera 30 is disposed at the end in the puncture assembly 40 away from the housing 11, i.e., the needle tip end of the puncture assembly 40. Thus the camera system can enter the body when the puncture begins, and the environment of the needle tip can be observed. Also, an observation angle of the user is matched with an operation angle, so that the puncturing operation can be manually performed directly with the observed content, without prolonging the reaction time, and the operation accuracy and efficiency are improved.

Optionally, the camera 30 is disposed at the end of the puncture assembly 40 away from the housing 11. i.e., the end of the puncture assembly 40 having the needle tip. Those skilled in the art can understand that the needle tip is used for puncturing the body tissues in the patient, and the camera 30 is disposed at the needle tip end of the puncture assembly 40, so as to photograph the body tissues, making a contact to the needle tip, of the patient.

Optionally, the camera 30 is disposed at one end, close to the needle tip, in the puncture needle 42 of the puncture assembly 40. During the puncturing operation, the camera 30 displays that the needle tip of the puncture needle 42 has reached a region where the operation needs to be performed, then puncturing is stopped, the puncture needle 42 is taken out, leaving the puncture sheath 41 in the body, and then other medical instruments are used through a middle channel in the puncture sheath 41 for the surgery.

Optionally, the display module 20 is located in the housing 11, with a compact structure, and synchronization between the observation angle and a puncturing action angle is high.

Optionally, the needle tip of the puncture assembly 40 is hollow, and the camera 30 is disposed in the hollow part of the needle tip. Since the needle tip is transparent, the camera 30 can photograph the specific situation of the tissues in the body at the needle tip through the transparent needle tip.

Optionally, a plane where the display module 20 is located forms an angle γ with an axial direction of the puncture assembly 40, where $85° \leq \gamma \leq 90°$. This angle range includes the best angle suitable for the user to view by human eyes during the puncturing operation, and there is no need to look up or look down to view the content displayed on the display module 20, which avoids unnecessary fatigue caused on the user viewing the display module 20.

In this embodiment, the user's line of sight can be focused to the tip of the puncture device 1 through the display module 20, so that the user has a better viewing angle while using the puncture device 1. The observation angle of the human eye, an operation angle and a lesion region punctured by the puncture needle 42 can achieve a better balanced and coordination state, and it is more convenient for the user to operate. The user can directly change a direction or perform other operations manually as soon as he/she sees the display screen 23; and the use efficiency is higher.

Optionally, the plane where the display module 20 is located may be set obliquely upward or downward, or an angle suitable for the human eyes to view may be set by the user according to a use scenario of the puncture device 1.

Figure 9:
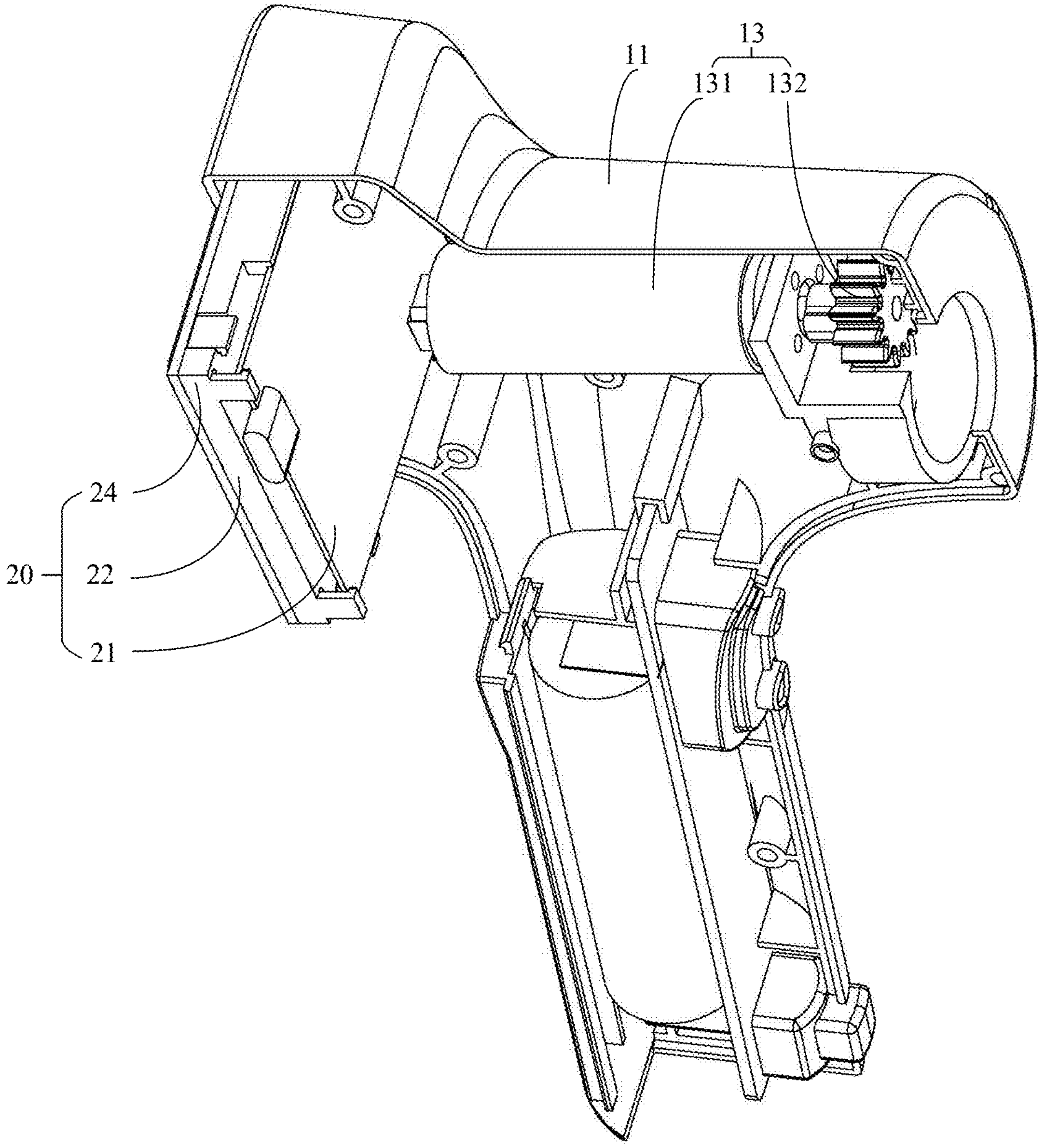
FIG. 9 is a schematic diagram of an internal structure of a puncture base of a puncture device according to an embodiment of the present application.
Figure 11:
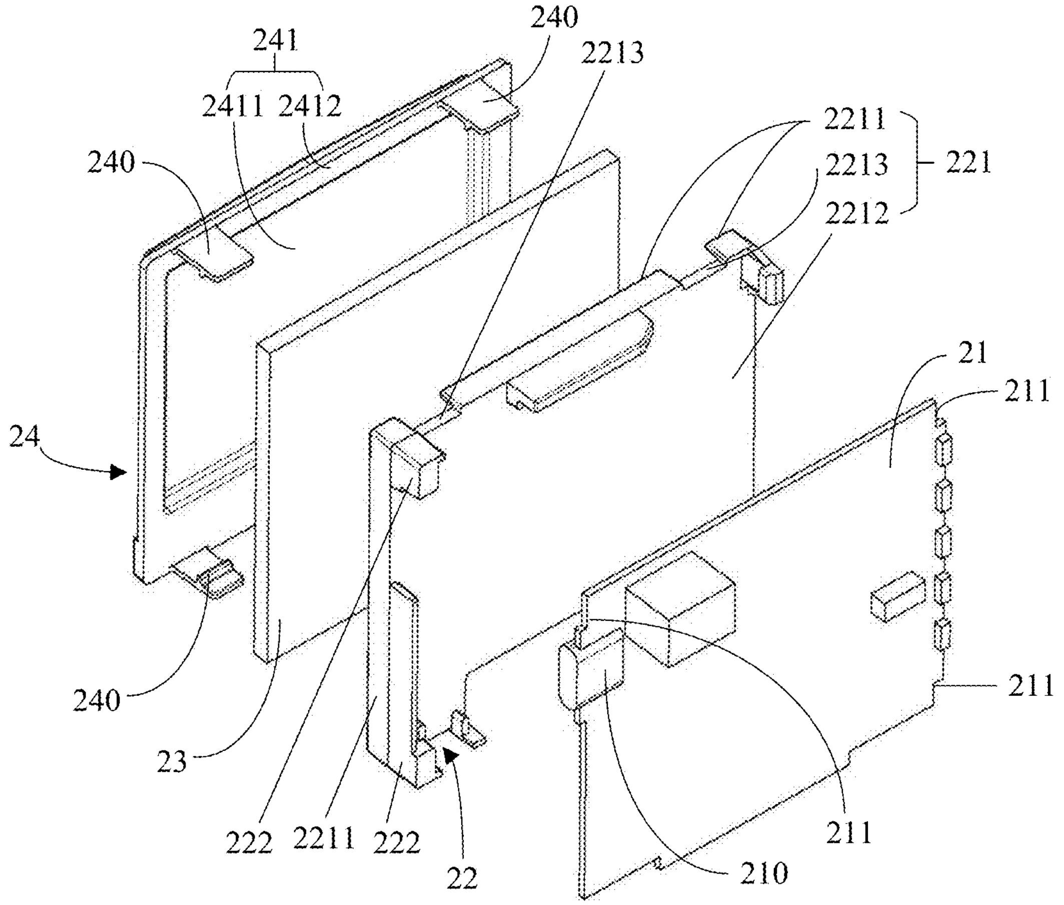
FIG. 11 is an explosion view of a display module of a puncture device according to an embodiment of the present application.

In some possible implementations, referring to FIGS. 9 and 11, the display module 20 includes a control circuit board 21, a fixed bracket 22, a display screen 23 and a protective cover plate 24.

The protective cover plate 24 is connected to the fixed bracket 22, and the display screen 23 is limited to the side of the fixed bracket 22 away from the puncture assembly 40.

The side of the fixed bracket 22 close to the puncture assembly 40 is connected to the control circuit board 21. The side of the protective cover plate 24 away from the fixed bracket 22 is connected to the inner side wall of the housing 11 of the puncture base 10.

In this embodiment, in the housing 11, one side of the protective cover plate 24 is connected to the inner side wall of the housing 11. The display module 20 is formed by stacking the control circuit board 21, the fixed bracket 22, the display screen 23 and the protective cover plate 24, where the protective cover plate 24 is connected with the fixed bracket 22, the display screen 23 is fixed between the protective cover plate 24 and the fixed bracket 22. A portion, corresponding to the display screen 23, of the protective cover plate 24 has a transparent structure, which is convenient for the user to see the content on the display screen 23 through the protective cover plate 24. The other edge of the fixed bracket 22 is connected to the control circuit board 21. Based on the arrangement according to this embodiment, a distribution order can be selected according to different functions of the display screen 23 and the control circuit board 21, and the layout is reasonable.

Figure 10:
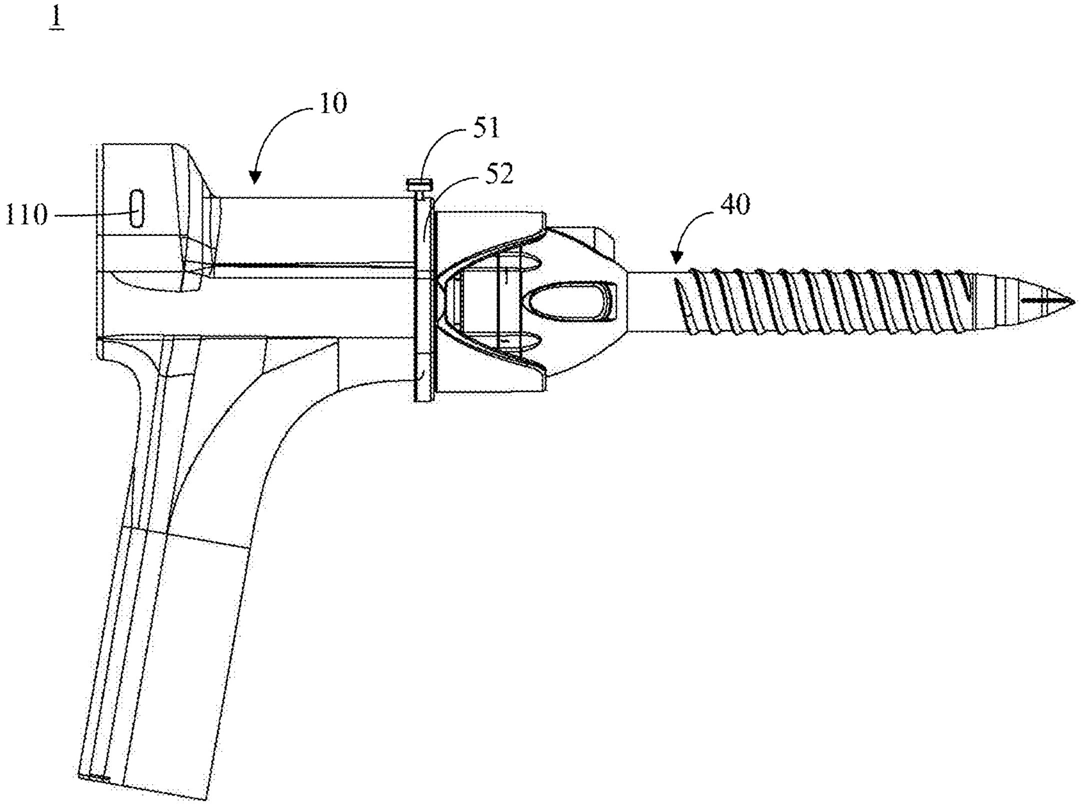
FIG. 10 is a schematic structural diagram of another puncture device according to an embodiment of the present application.

Optionally, referring to FIGS. 2, 10 and 11, a data transmission interface 210 is provided on one side of the control circuit board 21. An opening 110 is formed in the housing 11 of the puncture base 10. The data transmission interface 210 extends out of the control circuit board 21, and is embedded into the opening 110.

In this embodiment, acquired display data may be read through the data transmission interface 210, and a whole display device may also be powered by the data transmission interface 210. A battery may be built in the puncture base 10 to supply power to the display module 20 and the camera 30. After electricity stored in the battery is used up, the battery is charged through the data transmission interface 210 and store the electricity.

Optionally, the puncture base 10 may include a puncture base body used for accommodating the display module 20 and a handle used for the user to hold. The battery may further be accommodated in the handle according to a special shape of the handle.

Optionally, the battery may further be accommodated in the puncture base body portion. Optionally, the battery may further be powered by the driving mechanism 13 mentioned in the aforementioned examples. Optionally, a key is further provided on the side edge of the handle, the key can control circuit switches in the whole puncture device 1, and can be arranged at the handle to be convenient for the user to press.

In some possible implementations, the fixed bracket 22 includes a bracket body 221 and a first clamping key structure 222. The control circuit board 21 is provided with a first clamping position.

One end of the first clamping key structure 222 is connected to the bracket body 221. The other end of the first clamping key structure 222 is in clamping connection with the first clamping position in a mutual matching manner.

In this embodiment, the fixed bracket 22 may be in clamping connection with the control circuit board 21 through the first clamping key structure 222 and the first clamping position in the matching manner. The fixed bracket 22 and the control circuit board 21 can be fixed in such clamping connection way, and easy to be disassembled.

Optionally, a plurality of first clamping key structure 222 may be provided according to a usage condition; and correspondingly, a plurality of first clamping key positions 211 may further be provided. For example, the first clamping key structures 222 are arranged at four corners of the fixed bracket 22 respectively, and an equal number of first clamping key positions 211 are correspondingly arranged at four corners of the control circuit board 21 respectively, and clamping connection is performed at the four corners at the same time. At this time, the fixed bracket 22 is more stable to fix with the control circuit board 21.

Optionally, the fixed bracket 22 may further be fixedly connected to the control circuit board 21 in other ways, for example, through a bolt or welding.

In some possible implementations, the bracket body 221 includes a first baffle plate structure 2211 and a bottom plate 2212.

The first baffle plate structure 2211 is arranged in a circumferential direction of the bottom plate 2212 and abutted against the protective cover plate 24.

A placing region is formed by the first baffle plate structure 2211 and the bottom plate 2212 in an enclosing manner. The display screen 23 is embedded into the placing region.

In this embodiment, one side of the fixed bracket 22 is in clamping connection with the control circuit board 21, and the first baffle plate structure 2211 extends from the edge of the bracket body 221 on the other side of the fixed bracket 22. The first baffle plate structure 2211 may be a whole and fixed on the edge of the bracket body 221, or may further have a structure with a plurality of separate sub baffle plates, forming the placing region in the enclosing manner. The display screen 23 is embedded into the placing region, which prevents the display screen 23 from moving relative to the fixed bracket 22.

Optionally, the first baffle plate structures 2211 may be arranged in directions facing two sides of the fixed bracket 22. The first baffle plate structure 2211 on the left side of the fixed bracket 22 is used for fixing the display screen 23, and the first baffle plate structure 2211 on the other side may further be capable of fixing the control circuit board 21 at the same time.

Optionally, the first clamping key structure 222 and the first baffle plate structures 2211 may further be made integrally and arranged on the edge of the bottom plate 2212. Meanwhile, it is satisfied that the display screen 23 is fixed on the left side of the fixed bracket 22; and the control circuit board 21 is fixed on the right side of the fixed bracket 22.

Optionally, specific structures for the first clamping key structure 222 and the first baffle plate structures 2211 may be adaptively designed according to sizes of the display screen 23 and the control circuit board 21.

In some possible implementations, the protective cover plate 24 includes a cover plate body 241 and a second clamping key structure 240. The bracket body 221 is further provided with a second clamping key position 2213.

The second clamping key structure 240 has one end connected to the protective cover plate 24 and the other end in clamping connection with the second clamping key position 2213 in the mutual matching manner.

In this embodiment, the second clamping key structure 240 may be disposed on the edge of the cover plate body 241 and in clamping connection with one side of the fixed bracket 22 close to the display screen 23. As the first baffle plate structures 2211 are arranged on one side of the fixed bracket 22 close to the display screen 23, the display screen 23 is embedded into the first baffle plate structures 2211, and the side of the fixed bracket 22 close to the display screen 23 is in clamping connection with the protective cover plate 24. At this time, the cover plate body 241 is disposed on the other side of the display screen 23, capable of preventing the display screen 23 from falling off from the interior of the placing region formed by the first baffle plate structures 2211 in the enclosing manner. Also, as the display screen 23 has a display panel, there is a need for the display panel to clearly display a photographed content, and the protective cover plate 24 can further fulfill the effect of well protecting the display screen 23.

In some possible implementations, the cover plate body 241 includes a transparent member 2411 and a frame 2412. A display window is formed in one side of the housing 11 away from the puncture assembly 40.

The transparent member 2411 includes a part embedded into the frame 2412 and a part protruding from the frame 2412 and embedded into the display window.

In this embodiment, the cover plate body 241 includes the transparent member 2411 and the frame 2412. The transparent member 2411 is arranged corresponding to a displaying side of the display screen 23, which is convenient for the user to view the content displayed on the display screen 23. Since the whole display module 20 is disposed inside the housing 11 of the puncture base 10, in order to reasonably use the space in the housing 11 and take functions of various components into consideration at the same time, the protective cover plate 24 is located on a side surface close to the housing 11, i.e., the side of the housing 11 away from the puncture assembly 40. The display window is formed in a side surface of the housing 11 contacting the protective cover plate 24, and the transparent member 2411 is embedded into the display window which is a window region formed in the side surface of the housing 11. The transparent member 2411 may fulfill the protection effect itself, and thus material for preparing the housing 11 may be saved without adding any shell with the protection effect on the display window region on the side surface of the housing 11 contacting the protective cover plate 24.

Optionally, one side of the transparent member 2411 protrudes to be embedded into the display window of the housing 11, and correspondingly, the other side (i.e., one side close to the display screen 23) of the transparent member 2411 is provided with a depression. The display screen 23 comprises a part that may be embedded into the depression and a part disposed in the placing region of the fixed bracket 22. The display screen 23 is double fixed on the left and right sides, and thus such fixing way is better. Alternatively, the display screen 23 is embedded into the placing region, and a periphery of the display screen 23 makes a contact to the first baffle plate structures 2211. At this time, the display screen 23 and the first baffle plate structures 2211 are all embedded into the depression, which can also fulfill the better fixing effect.

Figure 12:
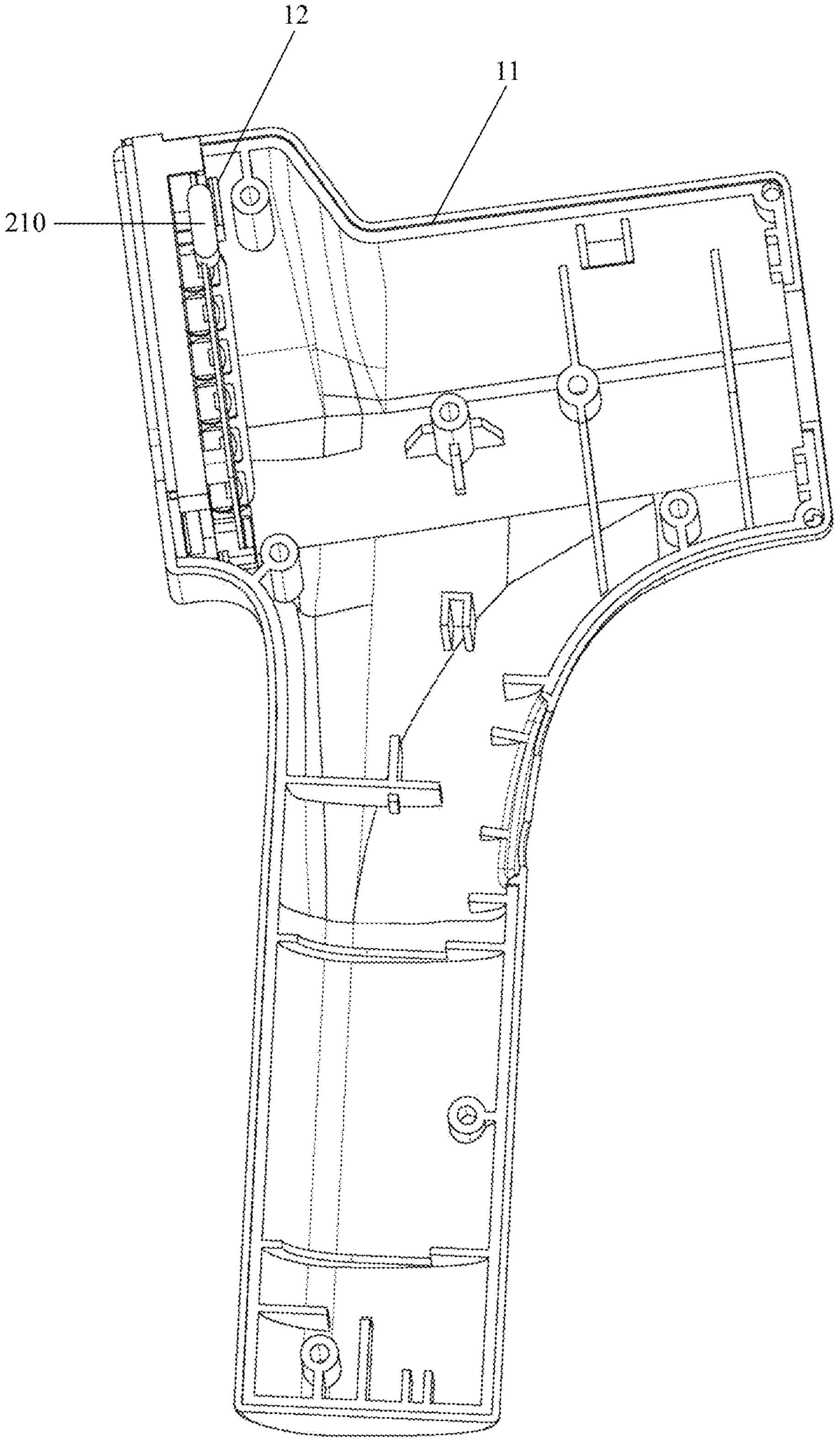
FIG. 12 is a schematic diagram of a positional relationship of a display module of a puncture device in a puncture base according to an embodiment of the present application.

Referring to FIG. 12, the puncture base 10 further includes a limiting stopper 12. The limiting stopper 12 is disposed on one side of the control circuit board 21 away from the fixed bracket 22. The limiting stopper 12 has one end connected to the housing 11 and the other end connected to the first clamping key structure 222.

In this embodiment, the whole display module 20 is positioned with the housing 11 on one side by being embedded into the display window of the housing 11 and on the other side through the limiting stopper 12. As being arranged at the outermost layer on the other side of the display module 20, the control circuit board 21 is in clamping connection with the fixed bracket 22 through the first clamping key structure 222. If the limiting stopper 12 is abutted against the control circuit board 21, the control circuit board 21 is affected by force applied by the limiting stopper 12, which may make the first clamping key structure 222 of the fixed bracket 22 separated from the first clamping key position 211 of the control circuit board 21. In order to ensure effective clamping connection between the control circuit board 21 and the fixed bracket 22, and ensure clamping connection between the first clamping key structure 222 and the first clamping position not to be affect, the limiting stopper 12 is abutted against the first clamping key structure 222 without directly making a contact to the control circuit board 21.

Optionally, a limiting rib extending toward a bottom end of the display module 20 is further arranged in the housing 11, and may drag the whole display module 20. The limiting rib makes a contact to the inner wall of the housing 11 at a top end of the display module 20. Therefore, the limiting rib is matched with the inner wall of the housing 11, and the display module 20 is fixed in the housing 11, which can avoid the display module 20 from falling off toward a lower part in the housing 11.

Optionally, the housing 11 is formed by coaptating a first housing 11 and a second housing 11. Contact surfaces of the first housing 11 and the second housing 11 are parallel to the plane where the axial direction of the puncture assembly 40 is located.

In this embodiment, the housing 11 is formed by coaptating the first housing 11 and the second housing 11, and the coaptated contact surfaces of the first housing 11 and the second housing 11 are parallel to the plane where the axial direction of the puncture assembly 40 is located. It may be understood that the first housing 11 and the second housing 11 are symmetric with respect to the axial direction of the puncture assembly 40. By applying such arrangement way between the first housing 11 and the second housing 11, the display module 20 may be very convenient to mount and disassemble. If there is a need for mounting and disassembling the display module 20, the first housing 11 is separated from the second housing 11, and then the display module 20 is taken out from or put into the housing 11 without forming an inlet for placing the display module 20 in the housing 11. Therefore, a positional relationship between the housing 11 and the display module 20 is reasonably used.

Optionally, corresponding connecting holes are formed in the first housing 11 and the second housing 11, and bolts are matched with the connecting holes, so that the first housing 11 is connected with the second housing 11 together.

Applying the embodiments of the present application at least has the following beneficial effects:

1. Quick disassembly/assembly between the puncture base 10 and the puncture assembly 40 can be achieved through the disassembling/assembling assembly 50, and in the case that the protective sleeve 60 is sleeved on the puncture base 10, the puncture assembly 40 can also be very convenient to disassemble/assemble.
2. The display module 20 is integrated into the puncture base 10 of the puncture device 1, and is convenient to disassemble/assemble.
3. The display module 20 is arranged on one side of the puncture base 10 close to the user, so that the user can view the content displayed on the display screen 23 while performing the puncturing operation using the puncture device 1.
4. The observation angle of the human eye, the operation angle and the lesion region punctured by the puncture needle 42 can achieve the better balanced and coordination state, so that the user is more convenient to operate, can directly change the direction or perform other operations manually as soon as he/she sees the display screen 23, and the use efficiency is higher.
5. The protective sleeve 60 fulfills the physical protection effect on the puncture base 10, so that the puncture base 10 can be reused without being chemically disinfected, and the service life of the puncture base 10 is prolonged.

Figure 16:
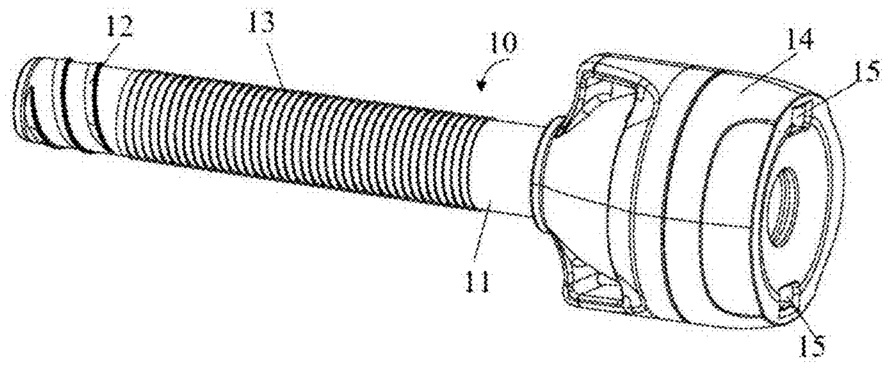
FIG. 16 is a schematic structural diagram of a sheath tube according to an embodiment of the present application.

Referring to FIG. 16, a sheath tube 10 includes a sheath tube body 11 a first thread structure 12 and a first horizontal stripe structure 13, where the first thread structure 12 and the first horizontal stripe structure 13 are disposed on an outer wall of the sheath tube body 11. The first thread structure 12 is arranged at a first end of the sheath tube body 11; the first horizontal stripe structure 13 is arranged between the first thread structure 12 and a second end 14 of the sheath tube body 11 in an axial direction of the sheath tube body 11; and horizontal stripes of the first horizontal stripe structure 13 are patterns perpendicular to the axial direction of the sheath tube body 11.

By applying the embodiments of the present application, at least the following beneficial effects can be achieved:

The first thread structure 12 is disposed on the outer wall of the first end, extending into the patient's body, of the sheath tube 10. Inclined patterns have the guiding effect and can weaken the friction force during puncturing, thereby reducing the difficulty of puncturing skin tissues, and reducing the difficulty of controlling the puncture strength of the sheath tube 10. Moreover, the first horizontal stripe structure 13 is disposed on the outer wall between the first thread structure 12 and the second end 14 away from the first end, in the axial direction of the sheath tube 10. The friction force between the sheath tube 10 and the incision tissues is strengthened by the horizontal patterns, which improves the stability of fixing the sheath tube on the incision. Therefore, it can effectively prevent the sheath tube 10 from being taken out when the instrument is changed, and avoid the incision from being damaged by the increased threads of the sheath tube.

What is claimed is:

1. A puncture device, comprising: a puncture base, a protective sleeve, a disassembling/assembling assembly and a puncture assembly, wherein a mounting hole is formed in one end of the protective sleeve;

the protective sleeve is sleeved on the puncture base;

the disassembling/assembling assembly is connected to the one end of the protective sleeve having the mounting hole; and a tip of the puncture assembly sequentially passes through the disassembling/assembling assembly and the mounting hole to be in detachable driving connection with the puncture base through the disassembling/assembling assembly, wherein the disassembling/assembling assembly comprises an elastic buckle connected to the protective sleeve;

the elastic buckle is provided with a deformation hole;

the tip of the puncture assembly sequentially passes through the deformation hole and the mounting hole, to be in detachable driving connection with the puncture base;

when the elastic buckle is in a state of not being subjected to an external force, a projection of the tip on a plane where the deformation hole is located partially overlaps with the deformation hole;

when the elastic buckle is in a state of being subjected to the external force, the projection of the tip on the plane where the deformation hole is located falls within the deformation hole;

wherein the elastic buckle comprises: a first deformation structure being elastically deformable, a second deformation structure being elastically deformable, and connecting arms being elongated and connecting an outer wall of the first deformation structure and an inner wall of the second deformation structure;

the first deformation structure is provided with a first through hole which forms the deformation hole;

the second deformation structure is provided with a second through hole; and a projection of the first deformation structure on a plane where the second deformation structure is located is in the second through hole, when the second deformation structure is subjected to an external force, the first deformation structure elastically deforms through the external force transmitted by the connecting arms, and when the second deformation structure is not subjected to an external force, the first deformation structure elastically restores.

2. The puncture device according to claim 1, wherein the connecting arms comprise a first connecting arm and a second connecting arm opposite to each other; and when the elastic buckle is in the state of not being subjected to the external force, the deformation hole is elliptical, projections of the first connecting arm and the second connecting arm on the plane where the deformation hole is located respectively form angles $\alpha$ with a straight line where a short axis of the deformation hole is located, wherein $0 \leq \alpha < 45°$.

3. The puncture device according to claim 2, wherein the elastic buckle further comprises: a fixed cover, a first handle and a supporting block, wherein the first handle and the supporting block are disposed opposite to each other;

the first handle and the supporting block are separately connected to the second deformation structure;

the fixed cover is provided with a third through hole corresponding to the deformation hole, and forms an accommodating region with one side of the puncture base close to the elastic buckle, and the elastic buckle is disposed in the accommodating region;

a first opening is formed in a peripheral of the fixed cover, the first handle passes through the first opening to extend out of the accommodating region, and one end of the supporting block is connected to the second deformation structure, and the other end of the supporting block being away from the second deformation structure is abutted against an inner side wall of the fixed cover.

4. The puncture device according to claim 3, wherein the disassembling/assembling assembly further comprises a limiting member including a first limiting block and a second limiting block;

the limiting member is fixedly connected to one side of the fixed cover close to the elastic buckle, the limiting member is disposed in the second through hole, and the first limiting block is used for limiting at least one of the first deformation structure and the second deformation structure and the second limiting block is used for limiting at least one of the first connecting arm and the second connecting arm, when the elastic buckle is deformed; and/or the limiting member is fixedly connected to one side of the protective sleeve close to the elastic buckle, the limiting member is disposed in the second through hole, and the first limiting block is used for limiting at least one of the first deformation structure and the second deformation structure and the second limiting block is used for limiting at least one of the first connecting arm and the second connecting arm, when the elastic buckle is deformed.

5. The puncture device according to claim 2, wherein the elastic buckle further comprises a first handle and a second handle disposed opposite to each other;

the first handle and the second handle are separately connected to the second deformation structure;

when the elastic buckle is in the state of not being subjected to the external force, projections of the first handle and the second handle on the plane where the deformation hole is located respectively form angles $\beta$ with a straight line where a long axis of the deformation hole is located, wherein $0 \leq \beta < 45°$; or when the elastic buckle is in the state of not being subjected to the external force, the projections of the first handle and the second handle on the plane where the deformation hole is located respectively form angles $\beta$ with the straight line where the short axis of the deformation hole is located, wherein $0 < \beta < 45°$.

6. The puncture device according to claim 5, wherein the disassembling/assembling assembly further comprises a fixed cover;

the fixed cover forms an accommodating region with a side of the puncture base close to the elastic buckle, and the elastic buckle is disposed in the accommodating region; and the fixed cover is provided with a third through hole corresponding to the deformation hole.

7. The puncture device according to claim 1, wherein the puncture base comprises a housing and a driving assembly;

the driving assembly is disposed in the housing and comprises a driving motor and a driving gear; and the tip of the puncture assembly is in driving connection with the driving assembly.

8. The puncture device according to claim 7, wherein the driving gear is fixedly connected to an output end of the driving motor; and a gear-tooth structure is disposed in a circumferential direction of the tip of the puncture assembly; and the driving gear is engaged with the gear-tooth structure.

9. The puncture device according to claim 8, wherein the puncture assembly comprises a connecting cover, a puncture needle and a puncture sheath;

the puncture sheath is sleeved outside the puncture needle;

a needle head end of the puncture needle extends out of a sheath head end of the puncture sheath, a needle tail end of the puncture needle and the tip are coaxial and fixedly connected to both sides of the connecting cover respectively; and the connecting cover is in driving connection with a sheath tail end of the puncture sheath.

10. The puncture device according to claim 9, wherein the connecting cover comprises a connecting plate, an extension sleeve and a clamping key;

both sides of the connecting plate are fixedly connected to the needle tail end of the puncture needle and the tip respectively;

the extension sleeve and the clamping key are fixedly connected to one side of the connecting plate facing the puncture sheath, separately;

the extension sleeve is sleeved outside the sheath tail end of the puncture sheath; and a clamping groove matching with the clamping key is formed in one side, facing the connecting plate, of the sheath tail end of the puncture sheath.

11. The puncture device according to claim 1, further comprising a display module and a camera;

the display module is disposed at one end of the puncture base away from the puncture assembly;

the camera is disposed at one end in the puncture assembly away from the puncture base; and the camera is in communication connection with the display module.

12. The puncture device according to claim 11, wherein the display module comprises a control circuit board, a fixed bracket, a display screen and a protective cover plate;

the protective cover plate is connected to the fixed bracket, and limits the display screen to one side of the fixed bracket away from the puncture assembly;

one side of the fixed bracket close to the puncture assembly is connected to the control circuit board; and one side of the protective cover plate away from the fixed bracket is connected to an inner side wall of a housing of the puncture base.

13. The puncture device according to claim 12, wherein the fixed bracket comprises a bracket body and a first clamping key structure; the control circuit board is provided with a first clamping position; and the first clamping key structure has one end connected to the bracket body and one other end in clamping connection with the first clamping position in a mutual matching manner.

14. The puncture device according to claim 13, wherein the bracket body comprises a first baffle plate structure and a bottom plate;

the first baffle plate structure is arranged in a circumferential direction of the bottom plate, and abutted against the protective cover plate; and a placing region is formed by the first baffle plate structure and the bottom plate in an enclosing manner; and the display screen is embedded into the placing region.

15. The puncture device according to claim 14, wherein the protective cover plate comprises a cover plate body and a second clamping key structure; the bracket body is further provided with a second clamping position; and the second clamping key structure has one end connected to the protective cover plate and one other end in clamping connection with the second clamping position in the mutual matching manner.

16. The puncture device according to claim 15, wherein the cover plate body comprises a transparent member and a frame; a display window is formed in one side of the housing away from the puncture assembly; and the transparent member has a part embedded into the frame and a part protruding from the frame and embedded into the display window.

17. The puncture device according to claim 16, wherein the puncture base further comprises a limiting stopper;

the limiting stopper is disposed on one side of the control circuit board away from the fixed bracket; and the limiting stopper has one end connected to the housing and one other end connected to the first clamping key structure.

18. The puncture device according to claim 1, wherein the puncture assembly comprises a sheath tube comprising a sheath tube body, a first thread structure and a first horizontal stripe structure, wherein the first thread structure and the first horizontal stripe structure are disposed on an outer wall of the sheath tube body;

the first thread structure is disposed at a first end of the sheath tube body; and the first horizontal stripe structure is disposed between the first thread structure and a second end of the sheath tube body in an axial direction of the sheath tube body; and horizontal stripes of the first horizontal stripe structure are patterns perpendicular to the axial direction of the sheath tube body.

* * * * *